(12) United States Patent
Yan et al.

(10) Patent No.: US 10,543,169 B2
(45) Date of Patent: *Jan. 28, 2020

(54) USE OF IL-22 DIMER IN MANUFACTURE OF A MEDICAMENT FOR INTRAVENOUS ADMINISTRATION

(71) Applicant: Generon (Shanghai) Corporation Ltd., Shanghai (CN)

(72) Inventors: Xiaoqiang Yan, Shanghai (CN); Cheng Huang, Shanghai (CN); Dongdong Wu, Shanghai (CN); Kaiyang Tang, Shanghai (CN); Yuliang Huang, Shanghai (CN)

(73) Assignee: Generon (Shanghai) Corporation Ltd., Shanghai (CN)

( * ) Notice: Subject to any disclaimer, the term of this patent is extended or adjusted under 35 U.S.C. 154(b) by 11 days.

This patent is subject to a terminal disclaimer.

(21) Appl. No.: 15/034,859

(22) PCT Filed: Nov. 6, 2014

(86) PCT No.: PCT/CN2014/090520
§ 371 (c)(1),
(2) Date: May 5, 2016

(87) PCT Pub. No.: WO2015/067199
PCT Pub. Date: May 14, 2015

(65) Prior Publication Data
US 2016/0263020 A1    Sep. 15, 2016

(30) Foreign Application Priority Data

Nov. 7, 2013  (CN) .......................... 2013 1 0549838

(51) Int. Cl.
*A61K 38/20*    (2006.01)
*A61K 9/00*     (2006.01)
*C07K 14/54*    (2006.01)

(52) U.S. Cl.
CPC ............ *A61K 9/0019* (2013.01); *A61K 38/20* (2013.01); *C07K 14/54* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,399,216 A | 8/1983 | Axel et al. |
| 4,496,689 A | 1/1985 | Mitra |
| 4,640,835 A | 2/1987 | Shimizu et al. |
| 4,657,760 A | 4/1987 | Kung et al. |
| 4,670,417 A | 6/1987 | Iwasaki et al. |
| 4,683,195 A | 7/1987 | Mullis et al. |
| 4,683,202 A | 7/1987 | Mullis |
| 4,791,192 A | 12/1988 | Nakagawa et al. |
| 4,943,529 A | 7/1990 | Van den Berg et al. |
| 4,965,188 A | 10/1990 | Mullis et al. |
| 5,010,182 A | 4/1991 | Brake et al. |
| 5,206,344 A | 4/1993 | Katre et al. |
| 5,225,212 A | 7/1993 | Martin et al. |
| 5,428,130 A | 6/1995 | Capon et al. |
| 5,654,010 A | 8/1997 | Johnson et al. |
| 6,274,710 B1 | 8/2001 | Dumoutier et al. |
| 6,331,613 B1 | 12/2001 | Dumoutier et al. |
| 6,359,117 B1 | 3/2002 | Dumoutier et al. |
| 6,551,799 B2 | 4/2003 | Gurney et al. |
| 6,797,493 B2 | 9/2004 | Sun et al. |
| 7,226,591 B2 | 6/2007 | Gurney et al. |
| 7,307,161 B1 | 12/2007 | Jacobs et al. |
| 7,459,533 B2 | 12/2008 | Jacobs et al. |
| 7,585,646 B2 | 9/2009 | Jacobs et al. |
| 7,651,694 B2 | 1/2010 | Lee |
| 7,666,402 B2 | 2/2010 | Huang et al. |
| 7,696,158 B2 | 4/2010 | Huang et al. |
| 7,718,604 B2 | 5/2010 | Huang et al. |
| 7,972,833 B2 | 7/2011 | Dumoutier et al. |
| 8,048,984 B2 | 11/2011 | Jacobs et al. |
| 8,178,675 B2 | 5/2012 | Romantsev et al. |
| 8,945,528 B2 | 2/2015 | Yan et al. |
| 9,352,024 B2 | 5/2016 | Wu et al. |
| 9,629,898 B2 | 4/2017 | Yan et al. |
| 2002/0102723 A1 | 8/2002 | Gurney et al. |
| 2003/0100076 A1 | 5/2003 | Gurney et al. |
| 2007/0172457 A1 | 7/2007 | Ebner et al. |
| 2007/0207943 A1 | 9/2007 | Ebner et al. |
| 2009/0202475 A1 | 8/2009 | Abbas et al. |
| 2011/0091417 A1 | 4/2011 | Gurney et al. |
| 2011/0262385 A1 | 10/2011 | Huang et al. |
| 2011/0280828 A1 | 11/2011 | Abbas et al. |
| 2013/0171100 A1* | 7/2013 | Yan ........................ A61K 38/20 424/85.2 |
| 2014/0314711 A1 | 10/2014 | Scheer et al. |
| 2014/0377222 A1 | 12/2014 | Huang et al. |
| 2015/0147293 A1 | 5/2015 | Wu et al. |
| 2015/0202267 A1 | 6/2015 | Yan et al. |
| 2016/0271221 A1 | 9/2016 | Yan et al. |
| 2018/0028614 A1 | 2/2018 | Huang et al. |

FOREIGN PATENT DOCUMENTS

| | | |
|---|---|---|
| CA | 2695734 A1 | 2/2009 |
| CA | 2705007 A1 | 5/2009 |

(Continued)

OTHER PUBLICATIONS

Merck Manual; Metabolic Syndrome, Jan. 2018.*

(Continued)

*Primary Examiner* — Joanna Hama
*Assistant Examiner* — Fozia Hamud
(74) *Attorney, Agent, or Firm* — Morrison & Foerster LLP

(57) ABSTRACT

The present application provides methods of administering an IL-22 dimer to an individual, such as a human individual, comprising intravenously administering to the individual an effective amount of an IL-22 dimer, wherein the amount of the IL-22 dimer is about 2 µg/kg to about 200 µg/kg (such as about 10 µg/kg to about 45 µ/kg), as well as methods of treating diseases by following such administration methods. Also provided are kits, unit dosages, and articles of manufacture for use in any one of the methods described herein.

16 Claims, 4 Drawing Sheets

Specification includes a Sequence Listing.

(56) References Cited

FOREIGN PATENT DOCUMENTS

| | | |
|---|---|---|
| CN | 1264596 A | 8/2000 |
| CN | 1381512 A | 11/2002 |
| CN | 101168049 A | 4/2008 |
| CN | 101218254 A | 7/2008 |
| CN | 101225110 A | 7/2008 |
| CN | 102380091 A | 3/2012 |
| CN | 103118699 A | 5/2013 |
| EP | 0 036 776 A2 | 9/1981 |
| EP | 0 073 657 A1 | 3/1983 |
| EP | 0 117 058 A2 | 8/1984 |
| EP | 0 117 060 A2 | 8/1984 |
| EP | 0 139 383 A1 | 5/1985 |
| EP | 0 183 070 A2 | 6/1986 |
| EP | 0 244 234 A2 | 11/1987 |
| EP | 0 362 179 A2 | 4/1990 |
| EP | 0 394 538 A1 | 10/1990 |
| EP | 0 402 226 A1 | 12/1990 |
| JP | 2008-508862 A | 3/2008 |
| JP | 2011-507863 A | 3/2011 |
| JP | 2013-536254 A | 9/2013 |
| WO | WO-97/03692 A1 | 2/1977 |
| WO | WO-1987/05330 A1 | 9/1987 |
| WO | WO-1989/05859 A1 | 6/1989 |
| WO | WO-1991/00357 A1 | 1/1991 |
| WO | WO-1995/013312 A1 | 5/1995 |
| WO | WO-1995/022419 A1 | 8/1995 |
| WO | WO-96/07399 A1 | 3/1996 |
| WO | WO-96/40072 A2 | 12/1996 |
| WO | WO-1999/32139 A1 | 7/1999 |
| WO | WO-99/61617 A1 | 12/1999 |
| WO | WO-02/029098 A2 | 4/2002 |
| WO | WO-2003/013589 A1 | 2/2003 |
| WO | WO-2006/000448 A2 | 1/2006 |
| WO | WO-2006/000448 A3 | 1/2006 |
| WO | WO-2006/073508 A1 | 7/2006 |
| WO | WO-2006/088833 A2 | 8/2006 |
| WO | WO-2006/088833 A3 | 8/2006 |
| WO | WO-2007/047796 A2 | 4/2007 |
| WO | WO-2007/115230 A2 | 10/2007 |
| WO | WO-2007/115230 A3 | 10/2007 |
| WO | WO-2009/020844 A1 | 2/2009 |
| WO | WO-2009/041734 A1 | 4/2009 |
| WO | WO-2009/062102 A2 | 5/2009 |
| WO | WO-2009/062102 A3 | 5/2009 |
| WO | WO-2009/079024 A1 | 6/2009 |
| WO | WO-2011/087986 A1 | 7/2011 |
| WO | WO-2012/028089 A1 | 3/2012 |
| WO | WO-2013/097748 A1 | 7/2013 |
| WO | WO-2014/145016 A2 | 9/2014 |
| WO | WO-2015/067198 A1 | 5/2015 |
| WO | WO-2015/067199 A1 | 5/2015 |
| WO | WO-2015/070077 A1 | 5/2015 |

OTHER PUBLICATIONS

Merck Manual; Fatty Liver, Jan. 2018.*
Adachi, M. et al. (2005). "Clinical Syndromes of Alcoholic Liver Disease," *Digestive Diseases* 23(3-4):255-263.
Asiedu, C. et al. (2007). "Cloning and Characterization of Recombinant Rhesus Macaque IL-10/Fc(ala-ala) Fusion Protein: A Potential Adjunct for Tolerance Induction Strategies," *Cytokine* 40:183-192.
Balthazar, E.J. et al. (Sep. 1985). "Acute Pancreatitis: Prognostic Value of CT," *Radiology* 156(3):767-772.
Balthazar, E.J. et al. (Feb. 1990). "Acute Pancreatitis: Value of CT in Establishing Prognosis," *Radiology* 174(2):331-336.
Banks, P.A. et al. (Oct. 2006). "Practice Guidelines in Acute Pancreatitis," *The American Journal of Gastroenterology* 101(10): 2379-2400.
Cobleigh, M.A. et al. (Jan. 2013). "Protective and Pathological Properties of IL-22 in Liver Disease: Implications for Viral Hepatitis," *Am. J. Pathology* 182(1):21-28.
Cox, G.N. et al. (2004). "Enhanced Circulating Half-Life and Hematopoietic Properties of a Human Granulocyte Colony-Stimulating Factor/Immunoglobulin Fusion Protein," *Exp. Hematol.* 32:441-449.
Dambacher, J. et al. (Mar. 2008). "The Role of Interleukin-22 in Hepatitis C Virus Infection," *Cytokine* 41(3):209-216.
De Oliveira Neto, M. et al. (Mar. 1, 2008; e-pub. Nov. 16, 2007). "Interleukin-22 Forms Dimers That are Recognized by Two Interleukin-22R1 Receptor Chains," *Biophys. J.* 94(5):1754-1765.
Dumoutier, L. et al. (Aug. 29, 2000). "Human Interleukin-10-Related T Cell-Derived Inducible Factor: Molecular Cloning and Functional Characterization as an Hepatocyte-Stimulating Factor," *PNAS* 97(18):10144-10149.
Dumoutier, L. et al. (Feb. 15, 2000). "Cloning and Characterization of IL-10-Related T Cell-Derived Inducible Factor (IL-TIF), a Novel Cytokine Structurally Related to IL-10 and Inducible by IL-9$^1$," *The Journal of Immunology* 164(4):1814-1819.
Eyerich, S. et al. (Sep. 2010; e-pub. Aug. 4, 2010). "IL-17 and IL-22: Siblings, Not Twins," *Trends Immunol.* 31(9):354-361.
Feng, D. et al. (2012). "Interleukin-22 Ameliorates Cerulein-Induced Pancreatitis in Mice by Inhibiting the Autophagic Pathway," *International Journal of Biological Sciences* 8(2):249-257.
Gao, B. (Apr. 2005). "Cytokines, STATs and Liver Disease," *Cell. Mol. Immunol.* 2(2):92-100.
Gill, H.K. et al. (Jan. 21, 2006). "Non-Alcoholic Fatty Liver Disease and the Metabolic Syndrome: Effects of Weight Loss and a Review of Popular Diets. Are Low Carbohydrate Diets the Answer?" *World Journal of Gastroenterology* 12(3):345-353.
Good, M. et al. (May 1, 2015). "The Role of IL-22 Signaling in the Pathogenesis of Necrotizing Enterocolitis (HUM1P.314)," *The Journal of Immunology* 194(Supplement 1): Abstract No. 52.39.
Hanash, A.M. et al. (Aug. 24, 2012). "Interleukin-22 Protects Intestinal Stem Cells from Immune-mediated Tissue Damage and Regulates Sensitivity to Graft Versus Host Disease," *Immunity* 37(2):339-350.
Henikoff, S. et al. (Nov. 15, 1992). "Amino Acid Substitution Matrices From Protein Blocks," *Proc. Nat'l Acad. Sci. USA* 89:10915-10919.
Hines, I.N. et al. (Jul. 9, 2004). "Recent Advances in Alcoholic Liver Disease III. Role of the Innate Immune Response in Alcoholic Hepatitis," *American Journal of Physiology—Gastrointestinal and Liver Physiology* 287(2):G310-G314.
Johnson, O.L. et al. (1996). "A Month-Long Effect from a Single Injection of Microencapsulated Human Growth Hormone," *Nature Medicine* 2:795-799.
Jones, B.C. et al. (Apr. 1, 2008; e-pub. Mar. 21, 2008). "Crystallization and Preliminary X-Ray Diffraction Analysis of Human IL-22 Bound to the Extracellular IL-22R1 Chain," *Acta Crystall. Sect. F. Structure Biol. Cryst. Commun.* 64(Pt. 4):266-269.
Klöppel, G. et al. (1991). "Chronic pancreatitis: evolution of the disease," *Hepato-gastroenterology* 38(5):408-412.
Kotenko, S.V. et al. (Sep. 8, 1995). "Interaction Between the Components of the Interferon γ Receptor Complex," *J. Biol. Chem.* 270(36):20915-20921.
Lei, K. et al. (May 19, 1995). "Structure-Function Analysis of Human Glucose-6-Phosphatese, the Enzyme Deficient in Glycogen Storage Disease Type 1a*," *The Journal of Biological Chemistry* 270(20):11882-11886.
Lewis, D.H. (1990). "Controlled Release of Bioactive Agents From Lactide/Glycolide Polymer," in Chapter 1 of *Biodegradable Polymers as Drug Delivery Systems*, Chasin, M. (ed.) et al., Marcel Dekker Inc. New York, 1990, pp. 1-41, fifty two pages.
Li, Q. (Sep. 2003). "Research Development of Interleukin-22," *Chinese J. of Cancer Biotherapy* 10(3):226-228 (Translation of Abstract Only).
Low, S.C. et al. (Jul. 2005). "Oral and pulmonary delivery of FSH-Fc fusion proteins via neonatal Fc receptor-mediated transcytosis," *Human Reproduction* 20(7):1805-1813.
Marchesini, G. et al. (Aug. 2001). "Nonalcoholic Fatty Liver Disease," *Diabetes* 50(8):1844-1850.
Matsusue K. et al. (Mar. 2003). "Liver-Specific Disruption of Pparγ in Lepiin-Deficient Mice Improves Fatty Liver But Aggravates Diabetic Phenotyps," *J. Clin. Invest.* 111(5): 737-747.

(56) References Cited

OTHER PUBLICATIONS

Max Bayard, M.D. et al. (Jun. 1, 2006). "Nonalcoholic Fatty Liver Disease," *American Family Physician* 73(11):1961-1968.

Mordenti, J. et al. (1989). "The Use of Interspecies Scaling in Toxicokinetics," in *Toxicokinetics and New Drug Development*, Yacobi A. ed. et al.; Pergamon Press, New York, pp. 42-96.

Mortele, K.J. et al. (Nov. 2004). "A Modified CT Severity Index for Evaluating Acute Pancreatitis: Improved Correlation With Patient Outcome," *American Journal of Roentgenology* 183:1261-1265.

Pan, H. et al. (Feb. 2004). "Hydrodynamic Gene Delivery of Interleukin-22 Protects the Mouse Liver from Concanavalin A-, Carbon Tetrachloride-, and Fas Ligand-Induced Injury Via Activation of STAT3," *Cell. Mol. Immunol.* 1(1):43-49.

Parks, O.B. et al. (Jan. 13, 2016). "Interleukin-22 Signaling in the Regulation of Intestinal Health and Disease," *Frontiers in Cell and Developmental Biology* 3:1-13(Article 85).

Radaeva, S. et al. (May 2004). "Interleukin 22 (IL-22) Plays a Protective Role in T Cell-mediated Murine Hepatitis: IL-22 Is a Survival Factor for Hepatocytes via STAT3 Activation," *Hepatology* 39(5):1332-1342.

Sambrook, J. et al. (1989). *Molecular Cloning—A Laboratory Manual*, 2$^{nd}$ Edition, Maniatis, T. ed. Et al., Cold Spring Harbor Laboratory Press, New York, NY pp. v-xxxii, twenty nine pages, (Table of Contents only).

Schmidt, J. et al. (Jan. 1992). "A Better Model of Acute Pancreatitis for Evaluating Therapy," *Annals of Surgery* 215(1):44-56.

Sugimoto, K. et al. (Feb. 2008). "IL-22 Ameliorates Intestinal Inflammation in a Mouse Model of Ulcerative Colitis," *The Journal of Clinical Investigation* 118(2): 534-544.

International Diabetes Federation. (2006). "The IDF Consensus Worldwide definition of the metabolic Syndrome."

Tymoczko, J.L. et al. (Dec. 23, 2011). "Membranes Define the Cell and Carry out Cellular Functions," Chapter 1.4 in *Biochemistry a Short Course*, Second Edition, W.H. Freeman and Company, New York, pp. 13-15, five pages.

WHO. (Jul. 2015). "What is Hepatitis?" located at <http://www.who.int/features/qa/76/en/>, last visited on Jan. 15, 2016, three pages.

Wolk, K. et al. (Jun. 2002). "Cutting edge: immune cells as sources and targets of the IL-10 family members?," *Journal of Immunology* 168(11):5397-5402.

Wu, C. et al. (Nov. 2007; e-pub. Oct. 14, 2007). "Simultaneous Targeting of Multiple Disease Mediators by a Dual-Variable-Domain Immunoglobulin," *Nat. Biotechnol.* 25(11):1290-1297.

Xie, M.H. et al. (Oct. 6, 2000; e-pub. Jun. 29, 2000). "Interleukin (IL)-22, a novel human cytokine that signals through the interferon receptor-related proteins CRF2-4 and IL-22R," *J. Biol. Chem.* 275(40):31335-31339.

Yang, R. et al. (Nov. 2012). "MR Imaging of Acute Pancreatitis: Correlation of Abdominal Wall Edema with Severity Scores," *European Journal of Radiology* 81(11):3041-3047.

Yasuda. (1993). *Biomedicine and Therapeutics* 27(10):1221-1223, (English translation of the Introduction only).

Zenewicz, L.A. et al. (Oct. 2007). "Interleukin-22 but Not Interleukin-17 Provides Protection to Hepatocytes during Acute Liver Inflammation," *Immunity* 27:647-659.

Zenewicz, L.A.et al. (2011). "Recent Advances in IL-22 Biology," *International Immunol.* 23(3):159-163.

Zheng, X.X. et al. (1995). "Administration of Noncytolytic IL-10/Fc in Murine Models of Lipopolysaccharide-Induced Septic Shock and Allogeneic Islet Transplantation," *J. Immunol.* 154(10):5590-5600.

Zhu, H. et al. (Nov. 12, 2004). "STAT3 Induces Anti-Hepatitis C Viral Activity in Liver Cells," *Biochem. Biophys. Res. Commun.* 324(2):518-528.

Zhu, Q. et al. (Nov. 2008). "Expression of rhEPO-L-Fc Fusion Protein and Analysis of its Bioactivity and Pharmacokinetics," *Sheng Wu Gong Cheng Xue Bao* 24(11):1874-1879 (English Abstract).

Canadian Office Action dated Jun. 28, 2017, for Canadian Application No. 2,809,900, filed on Feb. 28, 2013, four pages.

European Communication Pursuant to Article 94(3) EPC dated Nov. 28. 2016 for EP Application No. 11821115.0, filed on Aug. 30, 2011, four pages.

European Communication pursuant to Rules 161(2) and 162 EPC dated Aug. 22, 2016 for EP Application No. 14860301.2, filed on Nov. 6, 2014, two pages.

European Communication Under Rule 71(3) EPC dated Jul. 19, 2017 for EP Application No. 11821115.0, filed on Aug. 30, 2011, five pages.

European Supplementary Search Report dated Jul. 12, 2017 for EP Application No. 14860301.2 filed, on Jun. 7, 2016, seven pages.

European Supplementary Search Report dated Jun. 30, 2017 for EP Application No. 14860161.0, filed on Jun. 7, 2016, seven pages.

Extended European Search Report dated Oct. 10, 2014, for EP Patent Application No. 11821115.0, filed on Aug. 30, 2011, five pages.

International Search Report and Written Opinion dated Jun. 23, 2017 for PCT Application No. PCT/US2017/027806, filed on Apr. 14, 2017, twelve pages.

International Search Report dated Apr. 18, 2013, for PCT Patent Application No. PCT/CN2012/087694, filed on Dec. 27, 2012, four pages.

International Search Report dated Dec. 8, 2011 for PCT Patent Application No. PCT/CN2011/079124, filed on Aug. 30, 2011, four pages.

International Search Report dated Feb. 10, 2015 for International Application No. PCT/CN2014/090520 filed on Nov. 6, 2014, five pages.

International Search Report dated Jan. 30, 2015 for PCT Application No. PCT/CN2014/090519 filed Nov. 6, 2014, six pages.

International Search Report and Written Opinion dated Mar. 27, 2015 for PCT Application No. PCT/US2014/64655, filed on Nov. 7, 2014, sixteen pages.

Written Opinion of the International Searching Authority dated Feb. 10, 2015 for International Application No. PCT/CN2014/090520 filed on Nov. 6, 2014, four pages.

Written Opinion of the International Searching Authority dated Jan. 30, 2015 for PCT Application No. PCT/CN2014/090519 filed Nov. 6, 2014, five pages.

Written Opinion of the International Searching Authority dated Dec. 8, 2011 for PCT Patent Application No. PCT/CN2011/079124, filed on Aug. 30, 2011, seven pages.

Written Opinion of the International Searching Authority dated Apr. 18, 2013, for PCT Patent Application No. PCT/CN2012/087694, filed on Dec. 27, 2012, eleven pages.

U.S. Appl. No. 15/694,670, filed Sep. 1, 2017, by Huang et al.

Aujla, S.J. et al. (Mar. 2008, e-pub. Feb. 10, 2008). "IL-22 Mediates Mucosal Host Defense Against Gram-Negative Bacterial Pneumonia," *Nat Med* 14(3):275-281.

Ballance, D.J. et al. (Apr. 15, 1983). "Transformation of Aspergillus Nidulans by the Orotidine-5'-Phosphate Decarboxylase Gene of *Neurospora Crassa*," *Biochem. Biophys. Res. Commum.* 112(1):284-289.

Barker, N. et al. (Oct. 5, 2012). "Identifying the Stem Cell of the Intestinal Crypt: Strategies and Pitfalls," *Cell Stem Cell* 11:452-460.

Barker, N. et al. (Oct. 25, 2007, e-pub. Oct. 14, 2007). "Identification of Stem Cells in Small Intestine and Colon by Marker Gene Lgr5," *Nature* 449:1003-1007.

Beach, D. et al. (Mar. 12, 1981). "High-frequency Transformation of the Fission Yeast *Schizosaccharomyces pombe*," *Nature* 290:140-142.

Blazar, B. R., et al. (May 11, 2012). "Advances in Graft-Versus-Host Disease Biology and Therapy," *Nat Rev Immunol* 12(6):443-458.

Carmon, K.S. et al. (Jun. 2012; e-pub. Apr. 2, 2012). "LGR5 Interacts and Cointernalizes with Wnt Receptors to Modulate Wnt/β-Catenin Signaling," *Mol Cell Biol* 32(11):2054-2064.

Case, M. E. et al. (Oct. 1979)."Efficient Transformation of *Neurospora Crassa* by Utilizing Hybrid Plasmid DNA," *Proc. Natl. Acad. Sci. U. S. A.* 76(10):5259-5263.

Cella, M. et al. (Feb. 2009, e-pub. Nov. 2, 2008). "A Human Natural Killer Cell Subset Provides an Innate Source of IL-22 for Mucosal Immunity," *Nature* 457:722-725.

(56) References Cited

OTHER PUBLICATIONS

Chan, H.L-Y. et al. (Jun. 2007). "How Should We Manage Patients With Non-Alcoholic Fatty Liver Disease in 2007?" *Journal of Gastroenterology and Hepatology* 22(6):801-808.
Chang, A.C.Y. et al. (Oct. 19, 1978). "Phenotypic Expression in *E. coli* of a DNA Sequence Coding for Mouse Dihydrofolate Reductase," *Nature* 275(5681):617-624.
Choi, S. M. et al. (Mar. 2013). "Innate Stat3—Mediated Induction of the Antimicrobial Protein Reg3γ is Required for Host Defense Against MRSA Pneumonia," *J Exp Med* 210:551-561.
Clayburgh, D.R. et al. (Mar. 2004; e-published on Jan. 19, 2004). "A Porous Defense: the Leaky Epithelial Barrier in Intestinal Disease," *Lab Invest* 84(3):282-291.
Clinical Research (2006). vol. 83, No. 2, p. 238-242. (Cited in the Japanese Decision of Refusal dated Aug. 29, 2013 for Japanese Patent Application No. 2010-520208), ten pages. English translation of the relevant parts referred by the Examiner in the Decision of Refusal is being provided.
Das, R. et al. (Mar. 5, 2009). "Interleukin-23 Secretion by Donor Antigen-Presenting Cells is Critical for Organ-Specific Pathology in Graft-Versus-Host Disease," *Blood* 113(10):2352-2362.
De Boer et al. (Jan. 1983). "The tac Promotor: A Functional Hybrid Derived from the trp and lac Promotors," *Proc. Natl. Acad. Sci. USA* 80:21-25.
De Lau, W. et al. (Aug. 18, 2011). "Lgr5 Homologues Associate with Wnt Receptors and Mediate R-spondin Signalling," *Nature* 476:293-297.
Dimartino, J.F. et al. (Sep. 1999). "Mill Rearrangements in Haematological Malignancies: Lessons from Clinical and Biological Studies," *Br J Haematol.* 106(3):614-626.
EBI Accession No. AWL86673. (May 26, 2018). "Streptomyces Globisporus Elongation Factor Tu," Located at URL: <https://www.ebi.ac.uk/ena/data/view/AWL86673&display=text>, last visited on May 31, 2018.
Eriguchi, Y. et al. (Jul. 5, 2012, e-pub. Apr. 24, 2012). "Graft-Versus-Host Disease Disrupts Intestinal Microbial Ecology by Inhibiting Paneth Cell Production of α-Defensins," *Blood* 120(1):223-231.
Ferrara, J. L., et al. (May 2, 2009). "Graft-Versus-Host Disease," *Lancet* 373:1550-1561.
Fleer, R. et al. (Oct. 1, 1991). "Stable Multicopy Vectors for High-Level Secretion of Recombinant Human Serum Albumin by *Kluyveromyces* Yeasts," *Bio/Technology* 9(10):968-975.
Gao, H. et al. (Jun. 2006). "Long-Term Administration of Estradiol Decreases Expression of Hepatic Lipogenic Genes and Improves Insulin Sensitivity in ob/ob Mice: A Possible Mechanism Is through Direct Regulation of Signal Transducer and Activator of Transcription 3," *Molecular Endocrinology* 20(6):1287-1299.
Gerbitz, A. et al. (Jun. 1, 2004, e-pub. Feb. 12, 2004). "Probiotic Effects on Experimental Graft-Versus-Host Disease: Let Them Eat Yogurt," *Blood* 103(11):4365-4367.
Gething, M.J. et al. (Oct. 22, 1981). "Cell-Surface Expression of Influenza Haemagglutinin from a Cloned DNA the RNA Gene," *Nature*, 293:620-625.
Glinka, A. et al. (Sep. 30, 2011, e-pub. Sep. 9, 2011). "LGR4 and LGR5 are R-spondin Receptors Mediating Wnt/β-Catenin and Wnt/PCP Signalling," *EMBO Rep.* 12(10):1055-1061.
Goeddel, D.V. et al. (Oct. 18, 1979). "Direct Expression in *Escherichia coli* of a DNA Sequence Coding for Human Growth Hormone," *Nature* 281:544-548.
Goeddel, D.V. et al. (Sep. 25, 1980). "Synthesis of Human Fibroblast Interferon by *E. coli*," *Nucleic Acids Res.* 8(18):4057-4074.
Graham, F.L. et al. (1977). "Characteristics of a Human Cell Line Transformed by DNA from Human Adenovirus Type 5," *J. Gen Virol,* 36:59-72.
Graham, F.L. et al. (Apr. 1973). "A New Technique for the Assay of Infectivity of Human Adenovirus 5 DNA," *Virology* 52(2):456-467.
Grattagliano, I. et al. (May 2007). "Managing Nonalcoholic Fatty Liver Disease: Recommendations for Family Physicians," *Canadian Family Physician* 53(5):857-863.
Greenwald, R.B. et al. (Oct. 20, 1994). "Highly Water Soluble Taxol Derivatives: 2'-Polyethyleneglycol Esters as Potential Prodrugs," *Bioorg. Med.Chem. Lett.* 4(20):2465-2470.
Hess, B. et al. (1969). "Cooperation of Glycolytic Enzymes," *Adv Enzyme Regul.* 7:149-167.
Hill, G.R. et al. (May 1, 2000). "The Primacy of the Gastrointestinal Tract as a Target Organ of Acute Graft-Versus-Host Disease: Rationale for the use of Cytokine Shields in Allogeneic Bone Marrow Transplantation," *Blood* 95(9):2754-2759.
Hitzeman, R.A. et al. (Dec. 25, 1980). "Isolation and Characterization of the Yeast 3-Phosphoglycerokinase Gene (PKG) by an Immunological Screening Technique," *J. Biol. Chem.* 255(24):12073-12080.
Holland, J.P. (Nov. 14, 1978). "Isolation and Identification of Yeast Messenger Ribonucleic Acids Coding for Enolase, Glyceraldehyde-3-Phosphate Dehydrogenase, and Phosphoglycerate Kinase," *Biochemistry* 17(23):4900-4907.
Hong, F. et al. (Oct. 2004). "Interleukin 6 Alleviates Hepatic Steatosis and Ischemia/Reperfusion Injury in Mice with Fatty Liver Disease," *Hepatology* 40(4):933-941.
Hsiao, C.L. et al. (Aug. 1979). "High-Frequency Transformation of Yeast by Plasmids Containing the Cloned Yeast *ARG4 Gene,"* *Proc. Natl. Acad. Sci. (USA)* 76(8):3829-3833.
Hua, G. et al. (Nov. 2012, e-pub. Jul. 27, 2012). "Crypt Base Columnar Stem Cells in Small Intestines of Mice are Radioresistant," *Gastroenterology* 143:1266-1276.
Inoue, H. et al. (Feb. 2004; e-published on Jan. 11, 2004). "Role of STAT-3 in Regulation of Hepatic Gluconeogenic Genes and Carbohydrate Metabolism in Vivo," *Nat Med.* 10(2):168-174, (English Abstract only). English Replacement of: Inoue, H. et al. (Feb. 2004; e-published on Jan. 11, 2004). "Role of STAT-3 in Regulation of Hepatic Gluconeogenic Genes and Carbohydrate Metabolism in Vivo," *Experimental Medicine* 22(7):970-973.
Jenq, R.R. et al. (Mar. 2010; e-published on Feb. 19, 2010). "Allogeneic Haematopoietic Stem Cell Transplantation: Individualized Stem Cell and Immune Therapy of Cancer," *Nat Rev Cancer* 10(3)213-220; pp. 1-10 (advance publication).
Jenq, R.R. et al. (May 2012, e-pub. Apr. 30, 2012). "Regulation of Intestinal Inflammation by Microbiota Following Allogeneic Bone Marrow Transplantation," *The Journal of Experimental Medicine* 209(5):903-911.
Jones, E.W. (Jan. 1977). "Proteinase Mutants of *Saccharomyces cerevisiae,"* *Genetics* 85(1):23-33.
Kappel, L.W. et al. (Jan. 22, 2009, e-pub. Oct. 17, 2008). "IL-17 Contributes to CD4-Mediated Graft-Versus-Host Disease," *Blood* 113(4):945-952.
Kelly, J.M. et al. (Feb. 1985). "Transformation of *Aspergillus niger* by the amdS Gene of *Aspergillus nidulans,"* *EMBO J.* 4(2):475-479.
Keown, W.A. et al. (1990). "Methods for Introducing DNA into Mammalian Cells," *Methods in Enzymology* 185:527-537.
Kingsman, A.J. et al. (Oct. 1979). "Replication in *Saccharomyces cerevisiae* of Plasmid pBR313 Carrying DNA from the Yeast trpl Region," *Gene* 7(2):141-152.
Kolls, J. K., et al., (Nov. 2008). "Cytokine-Mediated Regulation of Antimicrobial Proteins," *Nat Rev Immunol,* 8(11):829-835.
Kreymborg, K. et al. (Dec. 2007). "IL-22 is Expressed by Th17 Cells in an IL-23-Dependent Fashion, but Not Required for the Development of Autoimmune Encephalomyelitis," *J Immunol* 179:8098-8104.
Krivtsov, A.V. et al. (Aug. 2006, e-pub. Jul. 16, 2006). "Transformation from Committed Progenitor to Leukaemia Stem Cell Initiated by MLL-AF9," *Nature.* 442(7104):818-822.
Levine, J.E. et al. (Aug. 22, 2013, e-pub. Jun. 12, 2013). "Low Paneth Cell Numbers at Onset of Gastrointestinal Graft-Versus-Host Disease Identify Patients at High Risk for Nonrelapse Mortality," *Blood* 122(8):1505-1509.
Louvencourt, L.D. et al. (May 1983). "Transformation of *Kluyveromyces lactis* by Killer Plasmid DNA," *J. Bacterial.* 154(2):737-742.
Mansour, S.L. et al. (Nov. 24, 1988). "Disruption of the Proto-Oncogene Int-2 in Mouse Embryo-Derived Stem Cells: A General Strategy for Targeting Mutations to Non-Selectable Genes," *Nature* 336:348-352.

(56) References Cited

OTHER PUBLICATIONS

Mantei, N. et al. (Sep. 6, 1979). "Rabbit β-globin mRNA Production in Mouse L Cells Transformed with Cloned Rabbit β-Globin Chromosomal DNA," *Nature* 281:40-46.

Mather, J.P. (Aug. 1980). "Establishment and Characterization of Two Distinct Mouse Testicular Epithelial Cell Lines," *Biol. Reprod.* 23(1):243-252.

Matthews, J. R. et al. (Dec. 2011). "Absolute Requirement for STAT3 Function in Small-Intestine Crypt Stem Cell Survival," *Cell Death Differ* 18:1934-1943.

Medema, J.P. et al. (Jun. 16, 2011). "Microenvironmental Regulation of Stem Cells in Intestinal Homeostasis and Cancer," *Nature* 474:318-326.

Nagalakshmi, M.L. et al. (May 2004). "Interleukin-22 Activates STAT3 and Induces IL-10 by Colon Epithelial Cells," *International Immunopharmacology* 4(5):679-691.

Pearson, C. et al. (Jun. 2012; e-published on May 10, 2012). "Lymphoid Microenvironments and Innate Lymphoid Cells in the Gut," *Trends Immunol* 33(6):289-296.

Peery, A. F. et al. (Nov. 2012, e-pub. Aug. 8, 2012). "Burden of Gastrointestinal Disease in the United States: 2012 Update," *Gastroenterology* 143:1179-1187.

Pickert, G. et al. (Jul. 2009, e-pub. Jun. 29, 2009). "STAT3 Links IL-22 Signaling in Intestinal Epithelial Cells to Mucosal Wound Healing," *J. Exp. Med.* 206:1465-1472.

Richter, W.F. et al. (Sep. 2012). "Mechanistic Determinants of Biotherapeutics Absorption Following SC Administration," *The AAPS Journal* 14(3):559-570.

Riley, P. et al. (Dec. 2007; e-published on May 4, 2007). "A Growing Burden: The Pathogenesis, Investigation and Management of Non-Alcoholic Fatty Liver Disease," *Journal of Clinical Pathology* 60(12):1384-1391.

Sale, G.E. (Mar. 1996). "Does Graft-Versus-Host Disease Attack Epithelial Stem Cells?," *Mol Med Today* 2(3):114-119.

Sanos, S. L. et al. (Mar. 2013, e-pub. Jan. 29, 2013). "Innate Lymphoid Cells: from Border Protection to the Initiation of Inflammatory Diseases," *Immunol Cell Biol* 91(3):215-224.

Sato, T. et al. (Jan. 20, 2011, e-pub. Nov. 28, 2010). "Paneth Cells Constitute the Niche for Lgr5 Stem Cells in Intestinal Crypts," *Nature* 469:415-418.

Sato, T. et al. (May 14, 2009; e-pub. Mar. 29, 2009). "Single Lgr5 Stem Cells Build Crypt-Villus Structures in Vitro without a Mesenchymal Niche," *Nature* 459:262-265.

Sawa, S. et al. (Apr. 2011, e-pub. Feb. 20, 2011). "RORγt+ Innate Lymphoid Cells Regulate Intestinal Homeostasis by Integrating Negative Signals from the Symbiotic Microbiota," *Nat Immunol* 12:320-326, thirty three pages.

Schroeder, M. A., et al. (May 2011). "Mouse Models of Graft-Versus-Host Disease: Advances and Limitations," *Dis Model Mech* 4(3):318-333.

Sekikawa, A. et al. (Mar. 2010, e-pub. Jan. 11, 2010). "Involvement of the IL-22/REG Lα Axis in Ulcerative Colitis," *Lab Invest* 90(3):496-505.

Shaw, C.H. et.al. (Sep. 1983). "A General Method for the Transfer of Cloned Genes to Plant Cells," *Gene* 23(3):315-330.

Shlomchik, E.D. (May 2007). "Graft-Versus-Host Disease," *Nat. Rev. Immunol.* 7(5):340-352.

Simons, B.D. et al. (Nov. 2011, e-pub. Jul. 20, 2011). "Stem Cell Self-Renewal in Intestinal Crypt," *Exp Cell Res.* 317(19):2719-2724.

Sonnenberg, G.F. et al. (Jan. 28, 2011, e-pub. Dec. 30, 2010). "CD4(+) Lymphoid Tissue-Inducer Cells Promote Innate Immunity in the Gut," *Immunity* 34(1):122-134.

Sonnenberg, G.F. et al. (May 2011, e-pub. Apr. 19, 2011). "Border Patrol: Regulation of Immunity, Inflammation and Tissue Homeostasis at Barrier Surfaces by IL-22," *Nat Immunol.* 12(5):383-390.

Spits, H. et al. (Feb. 2013; e-published on Jan. 7, 2013). "Innate Lymphoid Cells—A Proposal for Uniform Nomenclature," *Nat Rev Immunol* 13:145-149, advance online publication pp. 1-5.

Sreekrishna, K. et al. (1988). "High Level Expression of Heterologous Proteins in Methylotrophic Yeast *Pichia pastoris*," *J. Basic Microbial.* 28(4):265-278.

Stinchcomb, D.T. et al. (Nov. 1, 1979). "Isolation and Characterisation of a Yeast Chromosomal Replicator," *Nature* 282:39-43.

Stubbs, M.C. et al. (Jan. 2008, e-pub. Sep. 13, 2007). "MLL-AF9 and FLT3 Cooperation in Acute Myelogenous Leukemia: Development of a Model for Rapid Therapeutic Assessment," *Leukemia* 22:66-77.

Takashima, S. et al. (Feb. 14, 2011, e-pub. Jan. 31, 2011). "The Wnt Agonist R-Spondin1 Regulates Systemic Graft-Versus-Host Disease by Protecting Intestinal Stem Cells," *J Exp Med* 208(2):285-294.

Tilburn, J. et.al. (Dec. 1983). "Transformation by Integration in *Aspergillus nidulans*," *Gene* 26(2-3):205-221.

Tschemper, G. et al. (Jul. 1980). "Sequence of a Yeast DNA Fragment Containing a Chromosomal Replicator and the TRP1 Gene," *Gene* 10(2):157-166.

Tsunoda, S. et al. (May 1995). "Characterization of PEG-IL-6 and its Thrombopoetic Activity in Vivo," *Drug Delivery System* 10(3):175-180; (with English introduction).

Ueki, K. et al. (Jul. 13, 2004). "Central Role of Suppressors of Cytokine Signaling Proteins in Hepatic Steatosis, Insulin Resistance, and the Metabolic Syndrome in the Mouse," *PNAS* 101(28):10422-10427.

Urlaub, G. et al. (Jul. 1980). "Isolation of Chinese Hamster Cell Mutants Deficient in Dihydrofolate Reductase Activity," *Proc. Natl. Acad. Sci. USA* 77(7):4216-4220.

Van Den Berg, J.A. et al. (Feb. 1990). "*Kluyveromyces* as a Host for Heterologous Gene Expression: Expression and Secretion of Prochymosin," *Bio/Technology* 8(2):135-139.

Van Solingen, P. et al. (May 1977). "Fusion of Yeast Spheroplasts," *Journal of Bacteriology* 130(2):946-947.

Wang, F. et al. (Aug. 2013, e-published on May 2, 2013). "Isolation and Characterization of Intestinal Stem Cells Based on Surface Marker Combinations and Colony-Formation Assay," *Gastroenterology* 145:383-395.

Wingard, J.R. et al. (Jun. 1, 2011). "Long-Term Survival and Late Deaths after Allogeneic Hematopoietic Cell Transplantation," *J. Clin. Oncol.* 29(16):2230-2239.

Witte, E. et al. (Oct. 2010, e-published on Sep. 25, 2010). "Interleukin-22: A Cytokine Produced by T, NK and NKT Cell Subsets, with Importance in the Innate Immune Defense and Tissue Protection," *Cytokine Growth Factor Rev.* 21(5):365-379.

Wolk, K. et al. (May 2006). "IL-22 Regulates the Expression of Genes Responsible for Antimicrobial Defense, Cellular Differentiation, and Mobility in Keratinocytes: A Potential Role in Psoriasis," *Eur J Immunol.* 36:1309-1323.

Yang, L. et al. (Aug. 2010; e-published on Apr. 21, 2010). "Amelioration of High Fat Diet Induced Liver Lipogenesis and Hepatic Steatosis by Interleukin-22," *Journal of Hepatology* 53(2):339-347.

Yelton, M.M. et al. (Mar. 1, 1984). "Transformation of *Aspergillus nidulans* by Using a trpC Plasmid," *Proc. Natl. Acad. Sci. USA* 81(5):1470-1474.

You, M. et al. (Jul. 2004). "Recent Advances in Alcoholic Liver Disease-II. Minireview: Molecular Mechanisms of Alcoholic Fatty Liver," *Am J. Gastrointest Liver Physiol.* 287:GI-G6.

Yui, S. et al. (Apr. 2012; e-published on Mar. 11, 2012). "Functional Engraftment of Colon Epithelium Expanded in Vitro from a Single Adult Lgr5+ Stem Cell," *Nat Med* 18(4):618-624.

Zamecnik, P.C. et al. (Jun. 1, 1986). "Inhibition of Replication and Expression of Human T-Cell Lymphotropic Virus Type III in Cultured Cells by Exogenous Synthetic Oligonucleotides Complementary to Viral RNA," *Proc. Natl. Acad. Sci. USA* 83)12):4143-4146.

Zenewicz, L.A. et al. (Dec. 2008). "Innate and Adaptive Interleukin-22 Protects Mice from Inflammatory Bowel Disease," *Immunity* 29(6)947-957.

Zheng, Y. et al. (Feb. 8, 2007, e-pub. Dec. 24, 2006). "Interleukin-22, a $T_H17$ Cytokine, Mediates IL-23-Induced Dermal Inflammation and Acanthosis," *Nature* 445:648-651.

(56) References Cited

OTHER PUBLICATIONS

Zheng, Y. et al. (Mar. 2008, e-pub. Feb. 10, 2008). "Interleukin-22 Mediates Early Host Defense Against Attaching and Effacing Bacterial Pathogens," *Nat Med* 14:282-289.

Zhou, W. J. et al. (Sep. 5, 2013). "Induction of Intestinal Stem Cells by R-Spondin 1 and Slit2 Augments Chemoradioprotection," *Nature* 501:107-111.

Extended European Search Report dated Mar. 13, 2018, for EP Patent Application No. 17210060.4, filed on Dec. 22, 2017, eight pages.

International Preliminary Examination Report Completed on Sep. 3, 2009 for PCT Application No. PCT/US2008/071859 filed on Aug. 1, 2008, four pages.

Written Opinion of the International Searching Authority dated Nov. 26, 2008 for PCT Application No. PCT/US2008/071859 filed on Aug. 1, 2008, five pages.

Adams, L.A. et al. (2006). "Treatment of Non-Alcoholic Fatty Liver Disease," *Postgrad Med J* 82:315-322.

Browning, J.D. et al. (Jul. 2004). "Molecular Mediators of Hepatic Steatosis and Liver Injury," *The Journal of Clinical Investigation* 114(2):147-152.

Caballero, F. et al. (2009). "Enhanced Free Cholestrol, SREBP-2 and StAR Expression in Human NASH," *Journal of Hepatology* 50:789-796.

Lieber, C.S. et al. (Mar. 1966). "Study of Agents for the Prevention of the Fatty Liver Produced by Prolonged Alcohol Intake," *Gastroenterology* 50(3):316-322.

Mavrelis, P.G. et al. (1983). "Hepatic Free Fatty Acids in Alcoholic Liver Disease and Morbid Obesity," *Hepatology* 3(2):226-231.

Yamaguchi, K. et al. (Jun. 2007). "Inhibiting Triglyceride Synthesis Improves Hepatic Steatosis but Exacerbates Liver Damage and Fibrosis in Obese Mice with Nonalcoholic Steatohepatitis," *Hepatology* 45(6):1366-1374.

Australian Office Action dated May 3, 2019 for AU Application No. 2014346051 filed on May 4, 2016, four pages.

Canadian Notice of Allowance dated May 1, 2018, for Canadian Application No. 2,809,900, filed on Feb. 28, 2013, one page.

Chinese Office Action dated Feb. 11, 2019, for CN Application No. 2014800611889 filed on May 6, 2016, fourteen pages. (Machine English Translation of the OA is provided).

European Notice of Allowance dated Feb. 13, 2019 for EP Application No. 14860161.0, filed on Jun. 7, 2016, five pages.

European Office Action dated Nov. 5, 2018 for EP Application No. 14860301.2 filed, on Jun. 7, 2016, three pages.

European Communication Pursuant to Article 94(3) EPC dated Jun. 15, 2018 for EP Application No. 14860161.0, filed on Jun. 7, 2016, five pages.

International Preliminary Report on Patentability dated Oct. 25, 2018 for PCT Application No. PCT/US2017/027806 filed on Apr. 14, 2017, seven pages.

Japanese Notice of Reasons for Rejection dated Jul. 24, 2018 for JP Application No. 2016-550931 filed on May 5, 2016, six pages.

Japanese Office Action dated Mar. 12, 2019 for JP Application No. 2016-550931 filed on May 5, 2016, seven pages.

U.S. Appl. No. 16/093,583, filed Oct. 12, 2018 by Kolls et al. (Copy not submitted herewith pursuant to the waiver of 37 C.F.R. § 1.98(a)(2)(iii) issued by the Office dated Sep. 21, 2004.).

\* cited by examiner

USE OF IL-22 DIMER IN MANUFACTURE OF A MEDICAMENT FOR INTRAVENOUS ADMINISTRATION

RELATED APPLICATIONS

This application is a National Phase application under 35 U.S.C. § 371 of International Application No. PCT/CN2014/090520 filed Nov. 6, 2014, which claims priority benefit to Chinese Patent Application No. 201310549838.1 filed on Nov. 7, 2013, the contents of which are incorporated herein by reference in its-their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 720622001100SEQLIST.txt, date recorded: May 3, 2016, size: 23 KB).

FIELD OF INVENTION

This invention relates to the area of biological and medical technologies, in particular, this invention relates to the use of IL-22 dimer in the manufacture of a medicament for intravenous administration.

BACKGROUND

Interleukin-22 (IL-22), also known as IL-10 related T cell-derived inducible factor (IL-TIF), is a glycoprotein expressed in and secreted from activated T cells and natural killer cells (NK cells). Activated T cells are mainly CD4+ cells, especially CD28 pathway activated $T_h1$ cells, $T_h17$ cells and $T_h22$ cells, among others. The expression of IL-22 mRNA was originally identified in IL-9 simulated T cells and mast cells in murine, as well as Concanavilin A (Con A) stimulated spleen cells (Dumoutier, et al., J. Immunology, 164:1814-1819, 2000). The human IL-22 mRNA is mainly expressed in peripheral T cells upon stimulation by anti-CD3 or Con A. Feng et al reported Interleukin-22 ameliorates cerulein-induced pancreatitis in mice (Int. J. Biol. Sci, 8(2), 249-257, 2012).

The disclosures of all publications, patents, patent applications and published patent applications referred to herein are hereby incorporated herein by reference in their entirety.

SUMMARY OF INVENTION

It is an object of the present invention to provide a use of IL-22 dimer in the manufacture of a medicament for intravenous administration.

In one aspect of the present invention, a use of interleukin-22 (IL-22) dimer in the manufacture of a medicament for intravenous administration is provided.

In some embodiments, the medicament is used for the treatment of a disease selected from the group consisting of: metabolic disease, fatty liver, viral hepatitis, MODS, neurological disorder, and pancreatitis.

In some embodiments, the IL-22 dimer is shown as Formula I:

M1-L-M2    I wherein,
M1 is a first monomer of IL-22,
M2 is a second monomer of IL-22, and
L is a linker connecting said first monomer and said second monomer and disposed therebetween.

In some embodiments, the IL-22 dimer retains the biological activity of IL-22 and has a serum half-life of longer than twice of that of either the first or the second monomer.

In some embodiments, the serum half-life of the IL-22 dimer is longer than three, five, or ten times of that of the first and/or the second monomer.

In a preferred embodiment, the linker L is selected from the group consisting of:
(i). a short peptide comprising 3 to 50 amino acids; and
(ii). a polypeptide of Formula II:

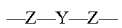

—Z—Y—Z—    II wherein,
Y is a carrier protein,
Z is nothing, or a short peptide(s) comprising 1 to 30 amino acids, and
"—" is a chemical bond or a covalent bond.

In some embodiments, the "—" is a peptide bond.
In some embodiments, Z is 5-50 amino acid residues in length.
In some embodiments, Z comprises the sequence of SEQ ID NO: 1 or SEQ ID NO: 10.
In some embodiments, Z has the sequence of SEQ ID NO: 1 or SEQ ID NO: 10.
In some embodiments, the carrier protein contains at least two cysteines capable of forming intermolecular disulfide bonds.
In some embodiments, the carrier protein is disposed at the N-terminal of IL-22 monomer.
In some embodiments, the carrier protein is disposed at the C-terminal of IL-22 monomer.
In some embodiments, the carrier protein is albumin or Fc fragment of human IgG.
In some embodiments, Fc fragment contains CH2 and CH3 domains.
In some embodiments, Fc fragment comprises the sequence of SEQ ID NO: 2 or SEQ ID NO: 9.
In some embodiments, Fc fragment has the sequence of SEQ ID NO: 2 or SEQ ID NO: 9.
In some embodiments, the IL-22 dimer is formed by two monomeric subunits wherein each monomeric subunit comprises an IL-22 domain, a dimerization domain and optionally a linker connecting the IL-22 domain and the dimerization domain.
In some embodiments, the IL-22 domain is IL-22 monomer, the dimerization domain comprises Fc fragment of human immunoglobulin (such as IgG1, IgG2, IgG3, or IgG4), the optional linker is a peptide connecting the IL-22 monomer and Fc fragment, and the dimer is formed by the connection of two dimerization domains (such as Fc Fragment) via one or more disulfide bond(s).
In some embodiments, the number of said disulfide bond is 2-4.
In some embodiments, the monomeric subunit of each IL-22 dimer comprises an amino acid sequence selected from SEQ ID NO: 4 and SEQ ID NOs: 6-8.
In some embodiments, the first monomer and the second monomer of the IL-22 dimer are identical.
In some embodiments, the first monomer and the second monomer are different.
In some embodiments, the biological activity of the IL-22 dimer is selected from one or more biological activities in a group consisting of:
(a) reducing the levels of amylase and/or lipase in vivo,
(b) ameliorating pancreatic edema in vivo,
(c) inhibiting necrosis of acinar cells and/or adipocytes in pancreas in vivo,
(d) ameliorating the infiltration of inflammatory cells in pancreas in vivo.

In some embodiments, the medicament is administered by the following ways: administering the IL-22 dimer at the amount of about 2 µg/kg to about 200 µg/kg, preferably at the amount of about 5 µg/kg to about 80 µg/kg IL-22 dimer, more preferably at the amount of about 10 µg/kg to about 45 µg/kg IL-22 dimer.

In a second aspect of the present invention, there is provided a method of administering an IL-22 dimer to an individual, comprising intravenously administering to the individual an effective amount of an IL-22 dimer, wherein the amount of the IL-22 dimer is about 2 µg/kg to about 200 µg/kg.

In a third aspect of the present invention, there is provided a method of treating diseases in an individual, comprising intravenously administering to the individual an effective amount of an IL-22 dimer, wherein the amount of the IL-22 dimer is about 2 µg/kg to about 200 µg/kg.

In some embodiments, the amount of the IL-22 dimer is about 5 µg/kg to about 80 µg/kg.

In some embodiments, the amount of the IL-22 dimer is about 10 µg/kg to about 45 µg/kg.

In some embodiments, the IL-22 dimer is administered no more than about once every week.

In some embodiments, the IL-22 dimer is administered no more than about once every month.

In some embodiments, the IL-22 dimer is administered no more than about once every three months.

In some embodiments, the IL-22 dimer comprises two monomeric subunits, wherein each monomeric subunit comprises an IL-22 domain and a dimerization domain.

In some embodiments, each monomeric subunit comprises an IL-22 domain linked to a dimerization domain via an optional linker sequence.

In some embodiments, the linker sequence is about 6 to about 30 amino acids.

In some embodiments, the linker sequence comprises the sequence of SEQ ID NO: 1.

In some embodiments, the linker sequence has the sequence of SEQ ID NO: 1.

In some embodiments, the dimerization domain comprises at least two cysteines capable of forming intermolecular disulfide bonds.

In some embodiments, the dimerization domain comprises at least a portion of the Fc fragment.

In some embodiments, the Fc fragment comprises CH2 and CH3 domains.

In some embodiments, the Fc fragment comprises the sequence of SEQ ID NO: 2.

In some embodiments, the Fc fragment has the sequence of SEQ ID NO: 2.

In some embodiments, the IL-22 domain of each monomeric subunit has the sequence of SEQ ID NO: 3.

In some embodiments, the each monomeric subunit has the sequence selected from SEQ ID NO: 4 and SEQ ID NOs: 6-8.

In some embodiments, the disease is selected from the group consisting of metabolic disease, fatty liver, viral hepatitis, MODS, neurological disorder, and pancreatitis.

In some embodiments, the individual is human.

It is clear for a skilled person in the art that, the technical features mentioned above and discussed in the examples below of the present invention could be combined with each other to result in a new or even better technical solution. Hence this invention should not be construed as limited to the embodiments set forth herein.

BRIEF DESCRIPTION OF FIGURES

As illustrated in FIG. 2A, the oval-shaped object labeled with "C" represents a carrier protein wherein the IL-22 is disposed at the N-terminal of the carrier protein. As illustrated in FIG. 2B, the half oval-shaped object labeled with "Fc" represents an Fc fragment which is a dimerizaion domain, showing a dimer is formed by the coupling of two Fc fragments via disulfide bond(s).

As illustrated in FIG. 3A, the oval-shaped object labeled with "C" represents a carrier protein wherein the IL-22 is disposed at the C-terminal of the carrier protein. As illustrated in FIG. 3B, the half oval-shaped object labeled with "Fc" represents an Fc fragment which is a dimerizaion domain, showing a dimer is formed by the coupling of two Fc fragments via disulfide bond(s).

DETAILED DESCRIPTION OF THE INVENTION

Figure 1:
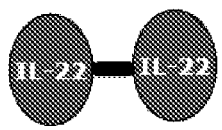
FIG. 1 is an illustration of an exemplary IL-22 dimer according to the present invention. In the figure, "—" represents a linker and the oval-shaped object labeled with "IL-22" represents an IL-22 monomer.

Upon an extensive and thorough study, the inventors have surprisingly found that IL-22 dimer has a outstanding effect in the manufacture of a medicament for intravenous administration. On this basis, this invention is achieved.

The present application provides methods of administering an IL-22 dimer by following a specific dosing regimen. The present application is based on the surprising finding that an IL-22 dimer, specifically, a dimeric complex of IL-22-Fc monomers, shows significantly lower toxicity when administered intravenously as compared to subcutaneous administration. Specifically, when a dimeric complex of IL-22-Fc monomers is administered subcutaneously to an individual at a dosage of about 2 µg/kg, delayed adverse events of the injection site, such as dry skin, erythema and nummular eczema were observed after dosing. On the other hand, the dimeric complex of IL-22-Fc monomers administered intravenously to an individual demonstrated excellent safety profile. No adverse event of the injection site and skin was observed at doses of about 2 or 10 µg/kg. Even at doses as high as 30-45 µg/kg, only limited adverse events such as dry skin, eye pruritus, erythematous rash were observed. Furthermore, the administration of IL-22 dimer does not lead to an increased serum level of an inflammatory cytokine in human.

Thus, the present application in one aspect provides methods of administering an IL-22 dimer to an individual (such as a human individual), comprising intravenously administering to the individual an effective amount of an IL-22 dimer, wherein the amount of the IL-22 dimer is about 2 µg/kg to about 200 µg/kg (such as about 10 µg/kg to about 45 µg/kg). In another aspect, there is provided a method of treating a disease in an individual (such as a human individual), comprising intravenously administering to the individual an effective amount of an IL-22 dimer, wherein the amount of the IL-22 dimer is about 2 µg/kg to about 200 µg/kg (such as about 10 µg/kg to about 45 µg/kg). Also provided are kits, unit dosages, and articles of manufacture for use in any one of the methods described herein.

Methods of the Present Invention

The methods described herein comprise administering an effective amount of an IL-22 dimer to an individual via intravenous administration. Suitable dosage of the IL-22 dimer includes, for example, about 2 µg/kg to about 200 µg/kg, including for example about 5 µg/kg to about 80 µg/kg, about 10 µg/kg to about 45 µg/kg, or about 30 to about 40 µg/kg. In some embodiments, the IL-22 dimer is administered intravenously at the dose of at least about any of 10 µg/kg, 20 µg/kg, 30 µg/kg, 40 µg/kg, or 50 µg/kg. In some embodiments, the IL-22 dimer is administered intravenously at the dose of no more than about any of 10 µg/kg, 20 µg/kg, 30 µg/kg, 40 µg/kg, or 50 µg/kg.

In some embodiments, there is provided a method of administering an IL-22 dimer to an individual (such as a human individual), comprising intravenously administering to the individual an IL-22 dimer, wherein the amount of the IL-22 dimer is about 10 µ/kg to about 45 µ/kg. In some embodiments, the amount of the IL-22 dimer is about 10 µ/kg to about 15 µ/kg, about 15 µ/kg to about 20 µ/kg, about 20 µ/kg to about 25 µ/kg, about 25 µ/kg to about 30 µ/kg, about 30 µ/kg to about 45 µ/kg. In some embodiments, the IL-22 dimer is administered at about 20 µ/kg to about 40 µ/kg, including for example about 30 µ/kg to about 35 µ/kg.

In some embodiments, the IL-22 dimer is administered once every week. In some embodiments, the IL-22 dimer is administered once every 2, 3, 4, 5, 6, 7, 8, 9, 10, 11, 12, or 24 weeks. In some embodiments, the IL-22 dimer is administered once every 1, 2, 3, 4, 5, 6, 7, 8, 9, 10, or 12 months. In some embodiments, the IL-22 dimer is administered only once. In some embodiments, the IL-22 dimer is administered no more frequently than once every week, once every month, once every two months, or once every six months.

In some embodiments, there is provided a method of administering an IL-22 dimer to an individual (such as a human individual), comprising intravenously administering to the individual an effective amount of an IL-22 dimer, wherein the amount of the IL-22 dimer is about 2 µ/kg to about 200 µ/kg (such as about 10 µ/kg to about 45 µ/kg). In some embodiments, there is provided a method of administering an IL-22 dimer to an individual (such as a human individual), comprising intravenously administering to the individual an effective amount of an IL-22 dimer, wherein the amount of the IL-22 dimer is about 2 µ/kg to about 200 µ/kg (such as about 10 µ/kg to about 45 µ/kg), wherein the IL-22 dimer is administered by intravenous push (IVP). In some embodiments, there is provided a method of administering an IL-22 dimer to an individual (such as a human individual, comprising intravenously administering to the individual an effective amount of an IL-22 dimer, wherein the amount of the IL-22 dimer is about 2 µ/kg to about 200 µg/kg (such as about 10 µ/kg to about 45 µ/kg), wherein the IL-22 dimer is administered by intravenous infusion. In some embodiments, there is provided a method of administering an IL-22 dimer to an individual (such as a human individual), comprising intravenously administering to the individual an effective amount of an IL-22 dimer, wherein the amount of the IL-22 dimer is about 2 µ/kg to about 200 µ/kg (such as about 10 µ/kg to about 45 µ/kg), wherein the IL-22 dimer is administered by continuous intravenous infusion.

In some embodiments, there is provided a method of administering an IL-22 dimer to an individual (such as a human individual), comprising intravenously administering to the individual an effective amount of an IL-22 dimer, wherein the amount of the IL-22 dimer is about 2 µ/kg to about 200 µ/kg (such as about 10 µ/kg to about 45 µ/kg). In some embodiments, there is provided a method of administering an IL-22 dimer to an individual (such as a human individual), comprising intravenously administering to the individual an effective amount of an IL-22 dimer, wherein the amount of the IL-22 dimer is about 2 µ/kg to about 200 µ/kg (such as about 10 µ/kg to about 45 µ/kg), wherein the IL-22 dimer is administered at least about once a week, for example at least about 2×, 3×, 4×, 5×, 6×, or 7× a week. In some embodiments, there is provided a method of administering an IL-22 dimer to an individual (such as a human individual), comprising intravenously administering to the individual an effective amount of an IL-22 dimer, wherein the amount of the IL-22 dimer is about 2 µ/kg/day to about 200 µ/kg/day (such as about 10 µ/kg/day to about 45 µ/kg/day), wherein the IL-22 dimer is administered continuously, for example via an infusion pump. In some embodiments, there is provided a method of administering an IL-22 dimer to an individual (such as a human individual), comprising intravenously administering to the individual an effective amount of an IL-22 dimer, wherein the amount of the IL-22 dimer is about 2 µ/kg to about 200 µ/kg (such as about 10 µ/kg to about 45 µ/kg), wherein the IL-22 dimer is administered no more than about once a week, for example no more than about any of once every two weeks, once every three weeks, once every four weeks, once every five weeks, once every six weeks, once every eight weeks, once every ten weeks, once every twelve weeks. In some embodiments, there is provided a method of administering an IL-22 dimer to an individual (such as a human individual), comprising intravenously administering to the individual an effective amount of an IL-22 dimer, wherein the amount of the IL-22 dimer is about 2 µ/kg to about 200 µ/kg (such as about 10 µ/kg to about 45 µ/kg), wherein the IL-22 dimer is administered no more than about once a month, for example no more than about any of once every two months, once every three months, once every four months, once every five months, once every six months, once every seven months, once every eleven months, once every twelve months. In some embodiments, the IL-22 dimer is administered no more than about once every 2, 3, 4, 5, 6, or 7 years.

The methods described herein can be useful for preventing and/or treating various diseases including but not limited to, metabolic disease, fatty liver, viral hepatitis, MODS (multiple organ dysfunction syndrome), neurological disorder, and pancreatitis.

In some embodiments, there is provided a method of treating a disease in an individual (such as a human individual), comprising intravenously administering to the individual an effective amount of an IL-22 dimer, wherein the amount of the IL-22 dimer is about 2 μ/kg to about 200 μ/kg (such as about 10 μ/kg to about 45 μ/kg). As used herein, the term "the individual to be treated" or "individual" refers to a mammal, such as human. An individual includes, but is not limited to, human, bovine, horse, feline, canine, rodent, or primate. In some embodiments, the individual is human.

In some embodiments, the individual to be treated is 16 years of age or younger, 18 years of age or younger, 25 years of age or younger, 35 years of age or younger, 45 years of age or younger, 55 years of age or younger, 65 years of age or younger, or 75 years of age or younger. In some embodiments, individual to be treated is 16 years of age or older, 18 years of age or older, 25 years of age or older, 35 years of age or older, 45 years of age or older, 55 years of age or older, 65 years of age or older, or 75 years of age or older.

In some embodiments, the individual administered with the IL-22 dimer does not show injection site reactions. In some embodiments, the individual administered with the IL-22 dimer does not show one or more of: dry skin, erythema, or nummular eczema, and/or significant abnormalities of the other safety evaluation indexes, such as physical examination, laboratory test, body weight, vital signs, electrocardiogram, and abdomen ultrasound.

In some embodiments, there is provided a method of treating a metabolic disease in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). Metabolic diseases that can be treated with the methods described herein include, but are not limited to, diabetes, hyperlipidemia and hyperglycemia. In some embodiments, there is provided a method of treating obesity in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, the IL-22 dimer is administered by intravenous infusion. In some embodiments, the IL-22 dimer is administered by intravenous push. In some embodiments, the IL-22 is administered by continuous intravenous infusion.

In some embodiments, there is provided a method of treating hyperlipidemia in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, there is provided a method of losing weight in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, the IL-22 dimer is administered by intravenous infusion. In some embodiments, the IL-22 dimer is administered by intravenous push. In some embodiments, the IL-22 is administered by continuous intravenous infusion.

In some embodiments, there is provided a method of improving glucose tolerance in an individual (such as a human individual), comprising intravenously administering to the individual an effective amount of an IL-22 dimer, wherein the amount of the IL-22 dimer is about 2 μg/kg to about 200 μg/kg (such as about 10 μg/kg to about 45 μg/kg). In some embodiments, there is provided a method of reducing adipocyte size in an individual (such as a human individual, for example an overweight human individual), comprising intravenously administering to the individual an effective amount of an IL-22 dimer, wherein the amount of the IL-22 dimer is about 2 μg/kg to about 200 μg/kg (such as about 10 μg/kg to about 45 μ/kg). In some embodiments, the IL-22 dimer is administered by intravenous infusion. In some embodiments, the IL-22 dimer is administered by intravenous push. In some embodiments, the IL-22 is administered by continuous intravenous infusion. In some embodiments, there is provided a method of treating fatty liver in an individual (such as a human individual), comprising intravenously administering to the individual an effective amount of an IL-22 dimer, wherein the amount of the IL-22 dimer is about 2 μ/kg to about 200 μ/kg (such as about 10 μ/kg to about 45 μ/kg). In some embodiments, there is provided a method of reducing deposition of triglyceride in an individual (such as human individual), comprising intravenously administering to the individual an effective amount of an IL-22 dimer, wherein the amount of the IL-22 dimer is about 2 μ/kg to about 200 μ/kg (such as about 10 μ/kg to about 45 μ/kg). In some embodiments, there is provided a method of reducing steatosis in an individual (such as a human individual), comprising intravenously administering to the individual an effective amount of an IL-22 dimer, wherein the amount of the IL-22 dimer is about 2 μ/kg to about 200 μ/kg (such as about 10 μ/kg to about 45 μ/kg). In some embodiments, the IL-22 dimer is administered by intravenous infusion. In some embodiments, the IL-22 dimer is administered by intravenous push. In some embodiments, the IL-22 is administered by continuous intravenous infusion.

Fatty liver is a disease in which excessive amounts of lipids accumulate in the liver cells. Normally lipids account for 3%-4% of the total weight of the liver. If the amount of lipid goes beyond 5%, a fatty liver forms. Lipids may comprise up to 40%-50% of the liver weight in severe fatty liver diseases. Fatty liver mainly comes from the disorder of lipid metabolism of the liver. The main form of lipid in the liver is triglyceride, which is characterized by macrovesicular steatosis. Fatty liver can lead to fibrosis of liver, cirrhosis and hepatocellular carcinoma. In some embodiments, the fatty liver to be treated is alcoholic fatty liver disease (AFLD), which is caused by excessive alcohol intake (greater than 20 g ethanol per day).

In some embodiments, the fatty liver to be treated is non-alcoholic fatty liver disease (NAFLD), including non-alcoholic fatty liver disease and steatohepatitis. In some embodiments, the NAFLD is obesity fatty liver, diabetic fatty liver, overnutritional or malnutritional fatty liver, fatty liver of pregnancy, drug induced fatty liver, fatty liver of hyperlipemia, and fatty liver of middle-aged and elderly. In some embodiments, the NAFLD is induced by metabolic syndrome including insulin resistance, lipid metabolism dysfunction and etc. In some embodiments, the NAFLD is induced indirectly by medicaments such as glucocorticoid, hormones, Tamoxifen, Methotrexate, Zidovudine, Aminodarone, acetylsalicylic acid (ASA), tetracycline, Didanosine, cocaine, perhexylene, hypervitaminosis A, diltizem; toxin such as, *Amanitaphalloides Lepiota*, Petrochemicals, phosphate, *Bacillus Cereus* toxin, organic solvent; indirect diseases induced such as, lipodystrophy, dysbetalipoproteinemia, Weber-Christian disease, Wolman's disease, acute fatty liver of pregnancy, Reye's syndrome; idiopathic immunodisease such as, inflammatory bowel disease (IBD), arthritis, lupus erythematosus; viral infection such as HIV, HBV; bacterial infections; or severe weight loss such as, starvation, gastric bypass, intestinal operation. In some embodiments, there is provided a method of treating viral hepatitis in an individual (such as a human individual), comprising intravenously administering to the individual an effective amount of an IL-22 dimer, wherein the amount of the IL-22 dimer is about 2 µ/kg to about 200 µg/kg (such as about 10 µ/kg to about 45 µ/kg). Viral hepatitis is an inflammation of the liver caused by hepatitis A, B, C, D, or E virus. In some embodiments, the viral hepatitis is any of hepatitis A, hepatitis B, hepatitis C, hepatitis D, hepatitis D, and hepatitis E. In some embodiments, the viral hepatitis is acute viral hepatitis. In some embodiments, the viral hepatitis is chronic hepatitis. In some embodiments, the IL-22 dimer is administered by intravenous infusion. In some embodiments, the IL-22 dimer is administered by intravenous push. In some embodiments, the IL-22 is administered by continuous intravenous infusion.

In some embodiments, there is provided a method of preventing the development of cirrhosis, liver failure, or liver cancer in an individual (such as a human individual) having viral hepatitis, comprising intravenously administering to the individual an effective amount of an IL-22 dimer, wherein the amount of the IL-22 dimer is about 2 µ/kg to about 200 µ/kg (such as about 10 µ/kg to about 45 µ/kg). In some embodiments, the IL-22 dimer is administered by intravenous infusion. In some embodiments, the IL-22 dimer is administered by intravenous push. In some embodiments, the IL-22 is administered by continuous intravenous infusion.

In some embodiments, there is provided a method of preventing liver tissue damage in an individual (such as a human individual), comprising intravenously administering to the individual an effective amount of an IL-22 dimer, wherein the amount of the IL-22 dimer is about 2 µ/kg to about 200 µ/kg (such as about 10 µ/kg to about 45 µ/kg). In some embodiments, there is provided a method of maintaining or decreasing the level of a hepatic enzyme (such as transaminase, for example aspartate aminotransferase or alanine aminotransferase) in an individual (such as a human individual), comprising intravenously administering to the individual an effective amount of an IL-22 dimer, wherein the amount of the IL-22 dimer is about 2 µ/kg to about 200 µ/kg (such as about 10 µ/kg to about 45 µ/kg). In some embodiments, the IL-22 dimer is administered by intravenous infusion. In some embodiments, the IL-22 dimer is administered by intravenous push. In some embodiments, the IL-22 is administered by continuous intravenous infusion.

In some embodiments, there is provided a method of treating multiple organ dysfunction syndrome (MODS) in an individual (such as a human individual), comprising intravenously administering to the individual an effective amount of an IL-22 dimer, wherein the amount of the IL-22 dimer is about 2 µ/kg to about 200 µg/kg (such as about 10 µ/kg to about 45 µ/kg). In some embodiments, the IL-22 dimer is administered by intravenous infusion. In some embodiments, the IL-22 dimer is administered by intravenous push. In some embodiments, the IL-22 is administered by continuous intravenous infusion.

Multiple organ dysfunction syndrome (MODS), previously known as multiple organ failure (MOF), is altered organ function in an acutely ill patient such that homeostasis cannot be maintained without medical intervention. MODS usually results from uncontrolled inflammatory response which is triggered by infection, injury (accident or surgery), hypoperfusion and/or hypermetabolism. The uncontrolled inflammatory response will lead to SIRS or sepsis. SIRS is an inflammatory state affecting the whole body. It is one of several conditions related to systemic inflammation, organ dysfunction, and organ failure. SIRS is a subset of cytokine storm, in which there is abnormal regulation of various cytokines. SIRS is also closely related to sepsis. When SIRS is due to an infection, it is considered as sepsis. Noninfectious causes of SIRS include trauma, burns, pancreatitis, ischemia and hemorrhage. Sepsis is a serious medical condition characterized by a whole-body inflammatory state. Sepsis can lead to septic shock, multiple organ dysfunction syndrome and death. Both SIRS and sepsis could ultimately progress to MODS.

Thus, in some embodiments, there is provided a method of treating SIRS in an individual (such as a human individual), comprising intravenously administering to the individual an effective amount of an IL-22 dimer, wherein the amount of the IL-22 dimer is about 2 µ/kg to about 200 µ/kg (such as about 10 µ/kg to about 45 µ/kg). In some embodiments, there is provided a method of treating MOF in an individual (such as human), comprising intravenously administering to the individual an effective amount of an IL-22 dimer, wherein the amount of the IL-22 dimer is about 2 µ/kg to about 200 µ/kg (such as about 10 µ/kg to about 45 µ/kg). In some embodiments, there is provided a method of treating sepsis in an individual (such as a human individual), comprising intravenously administering to the individual an effective amount of an IL-22 dimer, wherein the amount of the IL-22 dimer is about 2 µ/kg to about 200 µ/kg (such as about 10 µ/kg to about 45 µ/kg). In some embodiments, there is provided a method of treating liver failure in an individual (such as a human individual), comprising intravenously administering to the individual an effective amount of an IL-22 dimer, wherein the amount of the IL-22 dimer is about 2 µ/kg to about 200 µ/kg (such as about 10 µ/kg to about 45 µ/kg). In some embodiments, the MODS, SIRS, MOF, sepsis, or liver failure is caused by trauma, which includes, but is not limited to, traffic accident, burns, heart attack, and severe infective diseases.

In some embodiments, there is provided a method of treating a neurological disorder in an individual (such as a human individual), comprising intravenously administering to the individual an effective amount of an IL-22 dimer, wherein the amount of the IL-22 dimer is about 2 µ/kg to about 200 µ/kg (such as about 10 µ/kg to about 45 µ/kg). Suitable neurological diseases that can be treated with the methods of the present application include, but are not limited to, stroke, spinal cord injury, diseases associated with injured blood/brain barrier, and neurodegenerative diseases such as Alzheimer's disease, Parkinson's disease, Huntington's disease, amyotrophic lateral sclerosis, spinal muscular atrophy, spinal cerebellar and ataxias.

In some embodiments, there is provided a method of treating pancreatitis in an individual (such as a human individual), comprising intravenously administering to the individual an effective amount of an IL-22 dimer, wherein the amount of the IL-22 dimer is about 2 µ/kg to about 200 µ/kg (such as about 10 µ/kg to about 45 µ/kg). In some embodiments, the pancreatitis is selected from the group consisting of: acute pancreatitis, chronic pancreatitis, alcoholic pancreatitis, recurrent pancreatitis, bile reflux pancreatitis, interstitial pancreatitis, necrotizing pancreatitis, post ERCP pancreatitis.

IL-22

As used herein, the term "Interleukin-22" or "IL-22" refers to a protein, which (a) has essentially the same amino acid sequence as the human/murine IL-22 as described by Dumoutier et al. in U.S. Pat. No. 6,359,117 and (b) the same biological activity as natural IL-22. IL-22 of the present invention includes but is not limited to human IL-22, recombinant human IL-22, murine IL-22 and/or recombinant murine IL-22.

Specifically, Interleukin-22 (IL-22), also known as IL-10 related T cell-derived inducible factor (IL-TIF), is a glycoprotein expressed in and secreted from activated T cells and natural killer cells (NK cells). Activated T cells are mainly CD4+ cells, especially CD28 pathway activated $T_h1$ cells, $T_h17$ cells and $T_h22$ cells, among others. The expression of IL-22 mRNA was originally identified in IL-9 simulated T cells and mast cells in murine, as well as Concanavalin A (Con A) stimulated spleen cells (Dumoutier, et al., J. Immunology, 164:1814-1819, 2000). The human IL-22 mRNA is mainly expressed in peripheral T cells upon stimulation by anti-CD3 or Con A.

Native IL-22 precursor peptide consists of 179 amino acid residues, while the mature peptide consists of 146 amino acid residues. Dumoutier first reported the IL-22 cloned DNA sequences of mouse and human (Dumoutier, et al., 2000; U.S. Pat. Nos. 6,359,117 and 6,274,710). IL-22 is mainly expressed in activated T cells(especially Th17 cells), the lectin-stimulated spleen cells (Dumoutier JI 2000), IL-2/IL-12-stimulated NK cells (Wolk, K et al, J.Immunology, 168:5379-5402, 2002), and in a number of organs and tissues, including gut, liver, stomach, kidney, lung, heart, thymus, spleen, upon LPS stimulation, in which an increase of the expression of IL-22 in those organs and tissues can be measured. IL-22 expresses its biological function through the combination of IL-22R1 receptor and IL-10R2 receptor. IL-22R1 is a receptor specific to IL-22 and is expressed in skin, kidney, the digestive system (pancreas, small intestine, liver, large intestine, colon), and the respiratory system (lung, bronchi). Published researches demonstrated that IL-22 is an immuno-modulator.

IL-22 Dimer

Figure 2A:
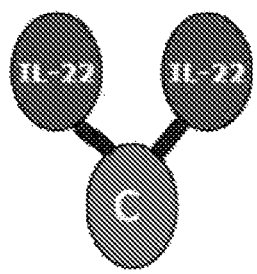
FIGS. 2A and 2B are illustrations of exemplary IL-22 dimers according to the present invention. In the figures, "—" represents an amino acid linker and the oval-shaped object labeled with "IL-22" represents an IL-22 monomer.
Figure 2B:
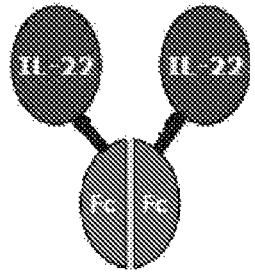
Figure 3A:
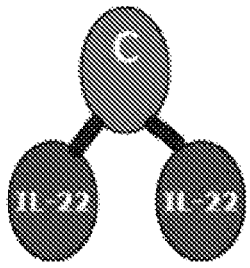
FIGS. 3A and 3B are illustrations of exemplary IL-22 dimers according to the present invention. In the figures, "—" represents an amino acid linker, the oval-shaped object labeled with "IL-22" represents an IL-22 monomer.
Figure 3B:
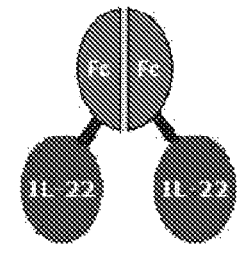

The structure of the IL-22 dimer of the present invention is exemplified as Formula I. FIGS. 1-3 illustrate the representative structures of the IL-22 dimer of the present invention, in which the carrier protein includes but is not limited to Fc fragment of human IgG (such as IgG1, IgG2, IgG3 or IgG4), or human albumin.

In some embodiments, the IL-22 dimer of the present invention comprises two monomeric subunits, in which each monomeric subunit comprises an IL-22 domain and a dimerization domain. Each of monomeric subunits comprises an IL-22 domain linked to a dimerization domain via an optional linker sequence. The IL-22 domain can be at the C terminus or N terminus of the dimerization domain. The carrier protein of the IL-22 dimer is formed by two dimerization domains via dimerization.

An amino acid sequence of the IL-22 dimer is shown in SEQ ID NO: 5 in which amino acid residues 1-146 represent IL-22, amino acid residues 147-162 represent the linker, and residues 163-308 represent another IL-22.

An amino acid sequence of an IL-22 monomer with Fc fragment, which is used to form the IL-22 dimer of this embodiment, is shown in SEQ ID NO: 4 in which amino acid residues 1-146 represent an IL-22, amino acid residues 147-162 represent the linker, and residues 163-385 represent Fc fragment of human IgG2. A dimer is formed by the two IL-22 monomers with Fc fragment via the coupling of the Fc fragments.

An amino acid sequence of an IL-22 monomer with Fc fragment, which is used to form the IL-22 dimer of this embodiment, is shown in SEQ ID NO: 6 in which amino acid residues 1-146 represent an IL-22, amino acid residues 147-152 represent the linker, and residues 153-375 represent Fc fragment of human IgG2. A dimer is formed by the two IL-22 monomers with Fc fragment via the coupling of the Fc fragments.

An amino acid sequence of an IL-22 monomer with Fc fragment, which is used to form the IL-22 dimer of this embodiment, is shown in SEQ ID NO: 7 in which amino acid residues 1-223 represent Fc fragment of human IgG2, amino residues 224-239 represent the linker, and residues 240-385 represent an IL-22. A dimer is formed by the two IL-22 monomers with Fc fragment via the coupling of the Fc fragments.

An amino acid sequence of an IL-22 monomer with Fc fragment, which is used to form the IL-22 dimer of this embodiment, is shown in SEQ ID NO: 8 in which amino acid residues 1-223 represent Fc fragment of human IgG2, amino acid residues 224-229 represent the linker, and residues 230-375 represent an IL-22. A dimer is formed by the two IL-22 monomers with Fc fragment via the coupling of the Fc fragments.

As used herein and in the claims, the term "linker peptide" or "linker" refers to oligo peptide disposed between one IL-22 monomer and carrier protein, or one IL-22 monomer (or IL-22 domain) and a dimerization domain and connecting the two domains together. There is no special restriction on the length of the linker. A linker is usually 5-50 amino acid residues in length. In general, a linker does not affect or significantly affect the proper fold and conformation formed by the configuration of the two IL-22 monomers. Some examples of linkers include (but are not limited to):

Preferably, the linker contains an amino acid sequence selected from:

(a). an amino acid sequence with 3-16 hydrophobic amino acid residues Gly or Pro, such as Gly-Pro-Gly-Pro-Gly-Pro;

(b). an amino acid sequence encoded by multiple cloning sites. Such sequences usually contain 5-20 amino acid residues, preferably, 10-20 amino acid residues;

(c). an amino acid sequence of a protein other than IL-22 monomer, such as an amino acid sequence of IgG or albumin; and (d). an amino acid sequence comprising any combination of (a), (b), and (c) above.

In one preferred embodiment, the linker has the sequence of GSGGGSGGGGSGGGGS (i.e. amino acid residues of SEQ ID NO: 1) and ASTKGP (i.e. amino acid residues of SEQ ID NO: 10).

In addition, an amino acid sequence not affecting the biological activity of IL-22 monomer can be added to the N-terminal or C-terminal of the fusion protein. In a preferred embodiment, such appended amino acid sequence is beneficial to expression (e.g. signal peptide), purification (e.g. 6×His sequence, the cleavage site of *Saccharomyces cerevi*- siae α-factor signal peptide (Glu-Lys-Arg), or enhancement of biological activity of the fusion protein.

In some embodiments, the IL-22 dimer comprises two monomeric subunits, wherein each monomeric subunit comprises an IL-22 domain and a dimerization domain. In some embodiments, the IL-22 domain is fused to the N-terminus of the dimerization domain. In some embodiments, the IL-22 domain is fused to the C-terminus of the dimerization domain. In some embodiments, the IL-22 domain and the dimerization domain are linked via an optional peptide linker (for example a peptide linker of about 5 to about 50 amino acids in length, for example a linker having the sequence of SEQ ID NO:10). In some embodiments, the dimerization domain of IL-22 dimer comprises leucine zippers.

In some embodiments, the IL-22 dimer comprises two IL-22 monomeric subunits, wherein each monomeric subunit comprises an IL-22 monomer and at least a portion of an immunoglobulin Fc fragment ("the Fc fragment", or namely Fc region). In some embodiments, the IL-22 domain is fused to the N-terminus of the Fc fragment. In some embodiments, the IL-22 domain is fused to the C-terminus of the Fc fragment. In some embodiments, the IL-22 domain and the Fc fragment are linked via an optional peptide linker (for example a peptide linker of about 5 to about 50 amino acids in length, for example a linker having the sequence of SEQ ID NO: 1 or SEQ ID NO: 10). In some embodiments, the IL-22 domain has the sequence of SEQ ID NO:3. In some embodiments, the Fc fragment comprises at least two cysteines capable of forming intermolecular disulfide bonds. In some embodiments, the Fc fragment is truncated at the N-terminus, e.g, lacks the first 1, 2, 3, 4, 5, 6, 7, 8, 9, or 10 amino acids of a complete immunoglobulin Fc domain. In some embodiments, the Fc fragment is of type IgG2. In some embodiments, the Fc fragment is of type IgG4. In some embodiments, the Fc fragment has the sequence of SEQ ID NO:2 or SEQ ID NO: 9.

In some embodiments, the IL-22 dimer comprises two IL-22 monomeric subunits, wherein each monomeric subunit comprises (for example has) the sequence of any of SEQ ID NO:4 or SEQ ID NOs: 6-8.

The invention encompasses modifications to the polypeptides described herein, including functionally equivalent proteins which do not significantly affect their properties and variants which have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, non-conservative mutations which do not significantly deleteriously change the functional activity, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an N-terminal methionyl residue or an epitope tag. Other insertional variants of the IL-22 monomeric subunits include the fusion to the N- or C-terminus of the polypeptide, or a polypeptide which increases the serum half-life of the IL-22 dimer.

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. In contrast, non-conservative amino acid substitutions tend to disrupt conformation and function of a protein. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). (See Table 1 below.)

TABLE 1

| Example of amino acid classification | |
| --- | --- |
| Small/Aliphatic residues: | Gly, Ala, Val, Leu, Ile |
| Cyclic Imino Acid: | Pro |
| Hydroxyl-containing Residues: | Ser, Thr |
| Acidic Residues: | Asp, Glu |
| Amide Residues: | Asn, Gln |
| Basic Residues: | Lys, Arg |
| Imidazole Residue: | His |
| Aromatic Residues: | Phe, Tyr, Trp |
| Sulfur-containing Residues: | Met, Cys |

In some embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., Biochemistry at pp. 13-15, 2nd ed. Lubert Stryer ed. (Stanford University); Henikoff et al., Proc. Nat'l Acad. Sci. USA (1992) 89:10915-10919; Lei et al., J. Biol. Chem. (1995) 270(20):11882-11886).

It was surprising found that although certain IL-22 dimers have less activities than IL-22 in in vitro assays, they are significantly more active in an in vivo context in treating pancreatitis. For example, in some embodiments, the IL-22 dimer described herein has an EC50 of no less than about 20 ng/mL (including for example no less than about any of 100 ng/mL, 200 ng/mL, 300 ng/mL, 400 ng/mL, or more) in an in vitro cell proliferation assay. In some embodiments, the IL-22 dimer has an EC50 that is at least about 5× (including for example at least about 10×, 30×, 50×, 100×, 150×, 300×, 400×, 500×, 600×, 1000× or more) that of a wildtype monomeric IL-22 (for example the monomeric IL-22 having the sequence of SEQ ID NO:3) in an in vitro cell proliferation assay. In some embodiments, the IL-22 dimer has an EC50 of no less than about 10 ng/mL (including for example no less than about any of 50 ng/mLl, 100 ng/mL, 200 ng/mL, 300 ng/mL, 400 ng/mL, or more) in an in vitro STAT3 stimulation assay. In some embodiments, the IL-22 dimer has an EC50 that is at least about 10× (including for example at least about 50×, 100×, 200×, 300×, 400×, 500×, 600×, 700×, 800×, 900×, 1000×, 1500×, or more) that of a wildtype monomeric IL-22 (for example the monomeric IL-22 having the sequence of SEQ ID NO:3) in an in vitro STAT3 stimulation assay.

In some embodiments, the IL-22 dimer has a serum half-life that is significantly longer than that of IL-22. In some embodiments, the IL-22 dimer as a serum half-life of at least about any of 15, 30, 50, 100, 150, 200, 250, 300, or 350 hours. In some embodiments, while the dose of IL-22 dimer is 2 μg/kg, the serum half-life is at least about any of 15, 30, 50, 100, 150, or 200 hours. In some embodiments, while the dose of IL-22 dimer is 10 μg/kg, the serum half-life is at least about any of 50, 100, 150, or 200 hours. In some embodiments, while the dose of IL-22 dimer is 30 μg/kg, the serum half-life is at least about any of 100, 150, 200, or 250 hours. In some embodiments, while the dose of IL-22 dimer is 45 μg/kg, the serum half-life is at least about any of 100, 150, 200, 250, 300, or 350 hours.

Preparation of IL-22 Dimers

The IL-22 monomeric subunits of the IL-22 dimers may be expressed using recombinant DNA technology. The nucleotide sequence encoding IL-22 monomeric subunits can be inserted into a replicable cloning or protein expression vector at restriction sites using known techniques. In some embodiments, a single nucleotide sequence encoding IL-22 monomeric subunits is inserted into a cloning or expression vector. In some embodiments, a nucleotide sequence encoding the IL-22 region and a nucleotide sequence encoding the extension peptide region may be separately inserted into a cloning or expression vector in such a manner that when the nucleotide sequence is expressed as a protein, a continuous polypeptide is formed. In some embodiments, a nucleotide sequence encoding a linker, a nucleotide sequence encoding a dimerization domain, and a nucleotide sequence encoding an IL-22 region may be separately inserted into a cloning or expression vector in such a manner that when the nucleotide sequence is expressed as a protein, a continuous polypeptide is formed. In some embodiments, the nucleotide sequence encoding IL-22 monomeric subunit may be fused to a nucleotide sequence encoding an affinity or identification tag, such as, but not limited to, a His-tag, FLAG-tag, SUMO-tag, GST-tag, antibody-tag, or MBP-tag. In some embodiments, the cloning or expression vector may be then transfected or transformed into eukaryotic or prokaryotic cells using known techniques. In some embodiments, IL-22 or IL-22 monomeric subunits may be expressed in vitro.

The expression host cell may be any cell able to express IL-22 dimers. Suitable prokaryotic expression host cells may include, but are not limited to, *Escherichia coli, Erwinia, Klesbsiella, Proteus, Salmonella, Serratia, Shigella, Bacillus subtilis, Bacillus licheniformis, Pseudomonas*, and *Streptomyces*. Eukaryotic cell, such as fungi or yeast, may also be suitable for expression of IL-22 monomeric subunits, for example, but not limited to, *Saccharomyces, Schizosaccharomyces pombe, Kluyveromyces lactis, Kluyveromyces fragilis, Kluyveromyces waltii, Kluyveromyces drosophilarum, Kluyveromyces thermotolerans, Kluyveromyces marxianus, Pichia pastoris, Neurospora crassa, Schwanniomyces, Penicillium, Tolypocladium, Synechococcus* and *Aspergillus*. Plant or algal cells may also be suitable for expression of IL-22 monomeric subunits, such as *Chlamydomonas*. Eukaryotic cell derived from multicellular organisms may also be suitable for expression of IL-22 monomeric subunits, for example, but not limited to, invertebrate cells such as *Drosophila* S2 and *Spodoptera* Sf9, or mammalian cells such as Chinese Hamster Ovary (CHO) cells, COS cells, human embryonic kidney cells (such as HEK293 cells), murine testis trophoblastic cells, human lung cells, and murine breast cancer cells. After the IL-22 monomeric subunit cloning plasmid is transformed or transfected into a host cell, the host cells can be grown on conventional nutrient media and protein expression induced, if necessary. In some embodiments, the expression of IL-22 monomeric subunits do not require inducement.

In some embodiments, expressed IL-22 monomeric subunits will form IL-22 dimers. In some embodiments, IL-22 monomeric subunits will require further inducement, such as by supplying an oxidation compound (such as hydrogen peroxide or a catalytic metal), UV light, or a chemical crosslinker (such as formaldehyde, 1,6-bismaleimidohexane, 1,3-dibromo-2-propanol, bis(2-chloroethyl)sulfide, or glutaraldehyde).

In some embodiments, the forming of IL-22 dimers do not require inducement. In some embodiments, host cell used to express IL-22 dimers is China Hamster Ovary (CHO cell). In some embodiments, IL-22 dimers may be purified using any number of protein purification techniques. For example, IL-22 dimers may be purified using affinity chromatography, ion exchange chromatography, reverse-phase HPLC, size-exclusion chromatography, precipitation, or ultracentrifugation. In some embodiments, an affinity tag fused to the IL-22 monomeric subunit polypeptide may be removed.

The preparation methods of IL-22 dimers can be referred to the patent application PCT/CN2011/079124 filed by Generon (Shanghai) Corporation, LTD on Aug. 30, 2011, incorporated herein by reference.

Kits and Medicines

Also provided are kits and medicines suitable for any one of the methods described herein. For example, in some embodiments, there is provided a kit comprising an IL-22 dimer and an instruction for administering the IL-22 dimer intravenously, for example at a dosage of about 2 μ/kg to about 200 μ/kg (such as about 10 μ/kg to about 45 μ/kg). In some embodiments, there is provided a unit dosage form for intravenous administration, wherein the unit dosage form comprises an effective amount of IL-22 dimer that would allow administration of the IL-22 dimer at a dosage of about 2 μ/kg to about 200 μ/kg (such as about 10 μ/kg to about 45 μ/kg). In some embodiments, there is provided a medicine comprising IL-22 dimer for intravenous administration, wherein the medicine comprises an effective amount of IL-22 dimer that would allow administration of the IL-22 dimer at a dosage of about 2 μ/kg to about 200 μ/kg (such as about 10 μ/kg to about 45 μ/kg). In some embodiments, there is provided a use of IL-22 dimer for the manufacture of a medicament for treating a disease, wherein the medicament is suitable for intravenous administration, and wherein the medicament comprises an effective amount of IL-22 dimer that would allow administration of IL-22 at a dosage of about 2 μ/kg to about 200 μ/kg (such as about 10 μ/kg to about 45 μ/kg).

The kit, medicine, medicament, and article of manufacture described herein can be provided in the form of vials (such as sealed vials), IV bags, and syringes.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

The following exemplary embodiments further describe the present invention. Although the description referred to particular embodiments, it will be clear to one skilled in the art that the present invention may be practiced with variation of these specific details. Hence this invention should not be construed as limited to the embodiments set forth herein. Further, for the embodiments in which details of the experimental methods are not described, such methods are carried out according to conventional conditions such as those described in Sambrook et al. Molecular Cloning: A Laboratory Manual (New York: Cold Spring Harbor Laboratory Press, 1989), or as suggested by the manufacturers.

EXAMPLES

Example 1

Proliferation Effect of IL-22 or IL-22 Dimer on Colo205 Cells

Colo205 cells were cultured in RPMI1640 10% FBS medium and the cells were grown to the logarithmic phase. Supernatant was discarded and PBS was added to wash away residual culture medium, followed by addition of 2-5 mL 0.25% Trypsin-EDTA for digestion. Then medium was added and mixed to uniformity by pipetting. Mixture was centrifuged at 1500 rpm for 5 min and cells were collected and prepared into $5.0*10^5$ Cell/ml cell suspension with basic medium. The suspension was added into the wells of 96-well plate (100 µL/well) and stayed overnight at 37° C., in 5% $CO_2$ incubator. On the next day, the 96-well plate was removed from the $CO_2$ incubator and centrifuged at 800 rpm for 5 minutes at 4° C. Then, 90 µL of cell supernatant was withdrawn from each well and 90 µL 0.1% BSA/RPMI 1640 was added to each well, followed by addition of IL-22 dimer (consisting of two monomeric subunits each comprising a sequence shown in SEQ ID NO: 4) to the final concentration of 1.4, 4.1, 12.3, 37.0, 111.1, 333.3, 1000, 3000 ng/mL, IL-22 (rhIL-22, namely, recombinant human IL-22) to the final concentration of 0.01, 0.04, 0.12, 0.37, 1.1, 3.3, 10, 30 ng/mL. The mixture was incubated for 20 hours at 37° C. in 5% $CO_2$ incubator and cell supernatant was collected and the OD value thereof was tested using IL-22 ELISA kit (R&D, Cat: S1000B).

Figure 4:
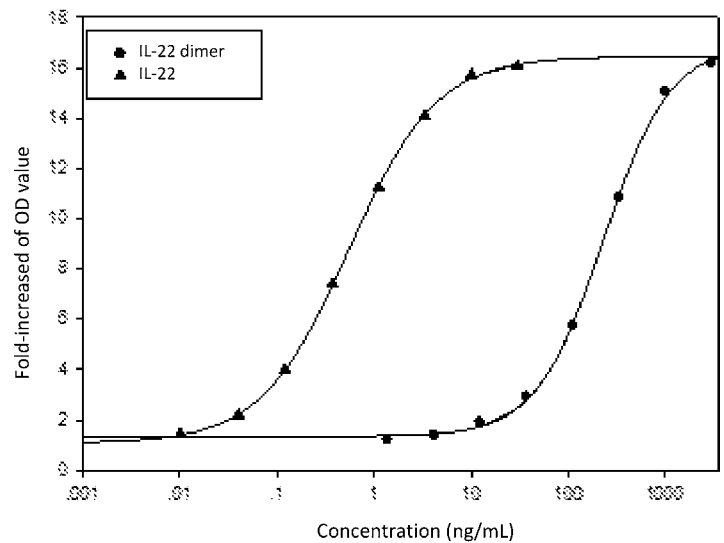
FIG. 4 shows the proliferative effect of IL-22 and IL-22 dimer on Colo205 cells in in vitro activity experiment.

As shown in FIG. 4, the half effective concentration (EC50) value of IL-22 dimer is 229 ng/mL (2,675 pM) and that of IL-22 is 0.54 ng/mL (32.4 pM). It shows that the bioactivity of IL-22 dimer is far lower than that of IL-22 monomer in in vitro activity experiment.

Example 2

Effect of IL-22 or IL-22 Dimer on STAT3 Activation in Colo205 Cells

Colo205 cells were cultured in RPMI1640 10% FBS medium and the cells were grown to the logarithmic phase. Supernatant was discarded and PBS was added to wash away residual culture medium, followed by addition of 2-5 mL 0.25% Trypsin-EDTA for digestion. Then medium was added and mixed to uniformity by pipetting. Mixture was centrifuged at 1500 rpm for 5 min and cells were collected and prepared into $2.0*10^5$ Cell/ml cell suspension with basic medium RPMI1640. The suspension was added into the wells of 96-well plate (100 µL/well) and stayed at 37° C. for 6 hrs, in 5% $CO_2$ incubator. The suspension was treated respectively with various concentrations of rhIL-22 or IL-22 dimer (consisting of two monomeric subunits each comprising a sequence shown in SEQ ID NO: 4) for 1 hr. After discarding the supernatant, add 40 µL cell lysis buffer (Cat No. 9803S, Cell Signalling) into each well. The supernatant was collected by centrifugation. Protein concentration was determined using Bradford method. Additionally, STAT3 phosphorylation level was measured using an ELISA method (STAT3 [pY705] phosphor ELISA kit (Invitrogen, Cat:KH00481). The pSTAT3 content is calculated by dividing the detected concentration of pSTAT3 by protein concentration.

Figure 5:
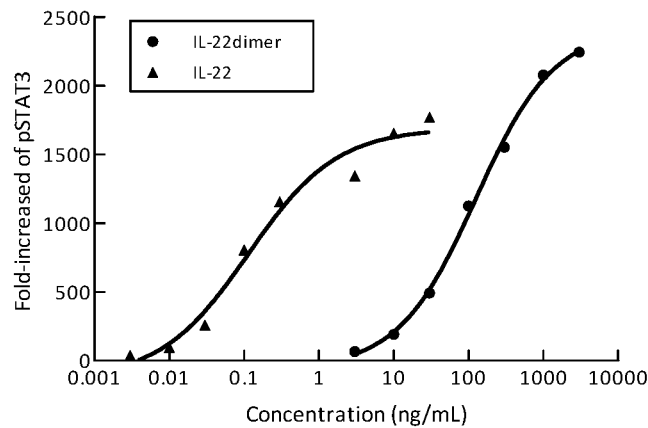
FIG. 5 shows the effect of IL-22 and IL-22 dimer on stimulating STAT3 in Colo205 cells in in vitro activity experiment.

As shown in FIG. 5, the half effective concentration (EC50) value of IL-22 dimer activating STAT3 is 119.5 ng/mL (1394 pM, calculated using the theoretical molecular weight of IL-22 dimer which is 85.7 KD) and that of IL-22 is 0.14 ng/mL (6.9 pM, calculated using the molecular weight of IL-22 which is 16.7 KD).

Example 3

Distribution of IL-22 Dimer in Organ Tissues in SD Rats

18 SD rats were randomly divided into 3 groups with 6 animals per group (half male and half female). The animals received a tail vein injection of $^{125}$I-IL-22 dimer labeled by Iodogen method (consisting of two monomeric subunits each comprising a sequence shown in SEQ ID NO: 4) at a dose of 30 µg/kg. The animals were sacrificed at 2, 24 and 48 hrs after the injection, respectively. The organ tissues were collected and weighed, and the radioactivity counts were measured directly. Then the radioactivity counts per gram of tissues were calculated.

Figure 6:
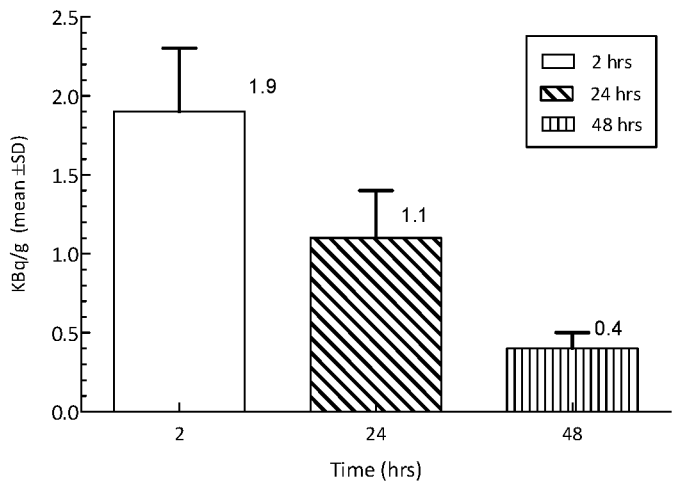
FIG. 6 shows the distribution of IL-22 dimer in pancreatic tissues in rats after administration. SD rats received a single intravenous injection of 30 µg/kg 125I labeled IL-22 dimer via cauda vein. The radioactivity counts in organ tissues were measured at 2, 24, and 48 hrs respectively after the injection.

The results showed that the IL-22 dimer was stable in pancreas for 48 hrs after the injection. As shown in FIG. 6, the concentrations of IL-22 dimer in pancreas at 24, 48 hrs were decreased to 56% and 21% of that of IL-22 dimer at 2 hrs after the injection, respectively. The concentrations of IL-22 dimer in livers at 24 hrs and 48 hrs were decreased to 28% and 9% of that of IL-22 dimer at 2 hrs after the injection, respectively. At 2 hrs after the injection, the concentrations of IL-22 dimer in pancreas were about ⅓ of that of IL-22 dimer in liver.

Example 4

Distribution of IL-22 Dimer in Organ Tissues in Cynomolgus Monkey 3 male cynomolgus monkeys, weighing 4.3-4.6 kg, received intravenous injection of IL-22 dimer (consisting of two monomeric subunits each comprising a sequence shown in SEQ ID NO: 4) at a dose of 100 µg/kg. The animals were sacrificed at 2 hrs after the injection. The organ tissues were collected and stored in liquid nitrogen. The tissues were weighed and lysed by adding the lysis buffer to obtain the tissue homogenate. After centrifugation, the supernatant was separated and subjected to protein concentration determination. The concentrations of IL-22 dimer in the tissues were measured using an ELISA method (Human IL-22 ELISA Kit, Biolegend, Cat. No 434506).

Figure 7:
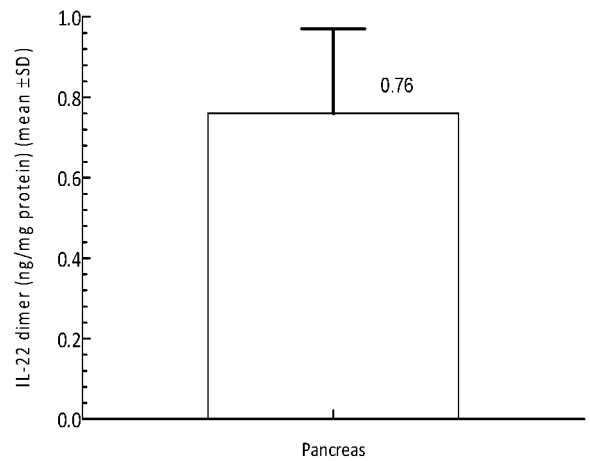
FIG. 7 shows the distribution of IL-22 dimer in pancreatic tissues in cynomolgus monkeys after administration. Cynomolgus monkeys received a single intravenous injection of 100 µg/kg IL-22 dimer. The drug concentrations in the organ tissues were measured at 2 hrs after the injection.

The results showed that the concentration of IL-22 dimer in the pancreas was fairly low (about 0.76 ng/mg protein). As shown in FIG. 7, this concentration was far lower than that of IL-22 dimer in liver (about ⅕ of the concentration in liver).

Example 5

Clinical Safety of IL-22 Dimer in Healthy Human Subject

Methods:

Healthy male volunteers were enrolled and randomized into 6 dose groups:

Placebo group (n=8): received a single dose of equal volume of 5% glucose/saline via intravenous infusion.

IL-22 dimer 2.0 μ/kg SC dose group (n=6)(SC group): received a single subcutaneous dose of IL-22 dimer at 2.0 μ/kg.

IL-22 dimer 2.0 μ/kg IV dose group (n=6)(IV group): IL-22 dimer were dissolved in 100 mL 5% glucose/saline solution and administered at a single dose of 2 μ/kg via intravenous infusion IL-22 dimer 10 μ/kg IV dose group (n=6)(IV group): IL-22 dimer were dissolved in 100 mL 5% glucose/saline solution and administered at a single dose of 10 μ/kg via intravenous infusion.

IL-22 dimer 30 μ/kg IV dose group (n=6)(IV group): IL-22 dimer were dissolved in 100 mL 5% glucose/saline solution and administered at a single dose of 30 μ/kg via intravenous infusion.

IL-22 dimer 45 μ/kg IV dose group (n=6)(IV group): IL-22 dimer were dissolved in 100 mL 5% glucose/saline solution and administered at a single dose of 45 μ/kg via intravenous infusion.

Wherein, the IL-22 dimer consisted of two monomeric subunits each comprising a sequence shown in SEQ ID NO: 4.

The safety was evaluated through physical examination, laboratory test, body weight, vital signs, electrocardiogram, and abdomen ultrasound, etc. In addition, the serum level of drug concentration, SAA-1, CRP, TG and cytokines were assayed.

Results:

A. Adverse Events

IL-22 dimer 2.0 μ/kg SC dose group: totally six adverse events considered related to the investigated drug, including injection site dry skin(×3), erythema(×2), and nummular eczema(×1).

IL-22 dimer 2.0 μ/kg IV dose group: no adverse events were observed.

IL-22 dimer 10 μ/kg IV dose group: two adverse events were observed, including chills (an infusion related reaction) (×1) and headache(×1).

IL-22 dimer 30 μ/kg IV dose group: six adverse events were observed, including local dry skin(×4), allergic dermatitis(×1), and infusion related reaction(×1).

IL-22 dimer 45 μ/kg IV dose group: twelve adverse events were observed, including local dry skin(6), eye pruritus (×3), erythematous rash (×2), and somnolence (×1).

Placebo group: adverse events including upper respiratory tract infection(×1), lethargy(×1) and hyperhidrosis (×1) were observed.

The results of adverse events, physical examination, laboratory test, body weight, vital signs, electrocardiogram, and abdomen ultrasound data, etc, showed that a single intravenous administration of IL-22 dimer at a dose as high as 45 μ/kg demonstrated a good safety profile with no observed serious adverse events or life-threatening adverse events. Fewer adverse events were reported following IL-22 dimer dosing via IV compared to SC at the 2.0 μ/kg dose level, indicating that IV was much better tolerated by the study subjects (Table 2). The results demonstrated that intravenous administration of IL-22 dimer has a better safety and tolerability compared to subcutaneous administration.

TABLE 2

Adverse events at injection site and skin after IL-22 dimer administration

| Dosing group | Injection site | skin |
| --- | --- | --- |
| placebo | Not observed | Not observed |
| 2 μg/kg, SC | dry skin (X3), erythema (X2), and nummular eczema (X1) were observed 10-17 days after the administration | Not observed |
| 2 μg/kg, IV | Not observed | Not observed |
| 10 μg/kg, IV | Not observed | Not observed |
| 30 μg/kg, IV | Not observed | Local dry skin (X4), allergic dermatitis (x1) |
| 45 μg/kg, IV | Not observed | Local dry skin (X6), eye pruritus (X3), erythematous rash (x2) |

B. Pharmacokinetics of IL-22 Dimer in Human

The vein blood samples were taken prior to the administration and at different time points following the administration. After centrifugation, the serum was separated and stored at <70° C. The drug concentration in the serum was measured using an ELISA method (Human IL-22 ELISA Kit, Biolegend, Cat. No 434506). Pharmacokinetic parameters were analyzed using a non-compartmental model on the detected results (analysis software: Phoenix™ WinNonlin® (Pharsight Corporation, Version 6.2.1). The results showed IL-22 dimer had a very excellent half-life in human, among which, the single dose of 45 μ/kg group had a half-life of 206 hrs which was significantly better than that of IL-22 monomer.

TABLE 3

Pharmacokinetic parameters (mean value, n = 6)

| Dosage (μg/kg, IV) | $T_{max}$ (hrs) | $C_{max}$ (ng/mL) | $T_{last}$ (hrs) | $C_{last}$ (ng/mL) | $AUC_{0-t}$ (hr * ng/mL) | $AUC_{0-\infty}$ (hr * ng/mL) | $AUC_{0-24h}$ (hr * ng/mL) | $T_{1/2}$ (hrs) | Cl (mL/hr/kg) | $V_Z$ (mL/kg) |
| --- | --- | --- | --- | --- | --- | --- | --- | --- | --- | --- |
| 2 | 0.7 | 15.5 | 60 | 3.75 | 437 | 650 | 247 | 39.4 | 3.35 | 177 |
| 10 | 0.2 | 62.3 | 284 | 4.41 | 4150 | 4840 | 1050 | 108 | 2.15 | 330 |

TABLE 3-continued

| Pharmacokinetic parameters (mean value, n = 6) | | | | | | | | | | |
|---|---|---|---|---|---|---|---|---|---|---|
| Dosage (μg/kg, IV) | $T_{max}$ (hrs) | $C_{max}$ (ng/mL) | $T_{last}$ (hrs) | $C_{last}$ (ng/mL) | $AUC_{0-t}$ (hr * ng/mL) | $AUC_{0-\infty}$ (hr * ng/mL) | $AUC_{0-24h}$ (hr * ng/mL) | $T_{1/2}$ (hrs) | Cl (mL/hr/kg) | $V_Z$ (mL/kg) |
| 30 | 0.2 | 176 | 528 | 6.12 | 15400 | 16900 | 3230 | 161 | 1.82 | 419 |
| 45 | 0.2 | 247 | 528 | 7.73 | 18000 | 20400 | 4340 | 206 | 2.26 | 654 |

C. IL-22 Dimer can Significantly Increase the Serum Levels of SAA, CRP and Decrease Serum Levels of TG a. Serum Amyloid Protein (SAA)

The concentration of serum SAA-1 was measured using an ELISA method (human SAA ELISA kit, Cat No. KHA0011C, Invitrogen).

Figure 8A:
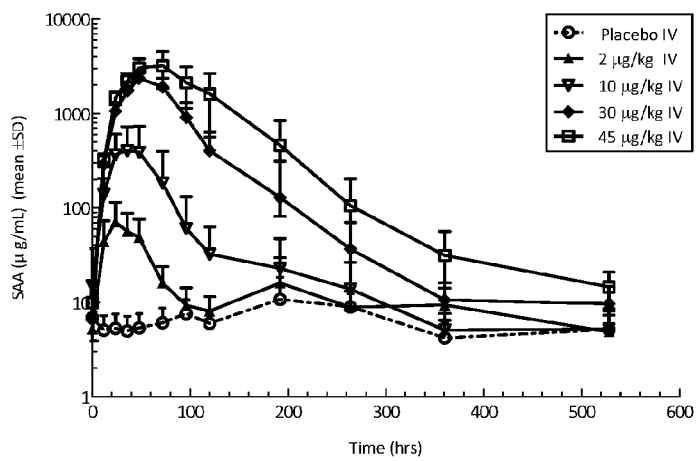
FIG. 8A shows the changes of the serum levels of amyloid protein (SAA) in human with the time after intravenous administration of IL-22 dimer.

The results showed the IV administration of IL-22 dimer can significantly increase the human serum concentration of SAA, indicating a very significant biological activity. As shown in FIG. 8A, compared to the placebo group, the concentration of SAA-1 was significantly increased at 12 hrs after the IL-22 dimer administration. High serum concentration of SAA remain fairly high in the 45 μ/kg dose group on day 15 after the administration.

TABLE 4

| the maximum concentration (Cmax) and fold-increased of SAA-1 | | |
|---|---|---|
| Group(IV) | SAA-1 Cmax (μg/kg) | Fold-increased of Cmax (relative to placebo group) |
| Placebo | 6* | 1 |
| IL-22 dimer 2 μg/kg, IV | 71 | 12 |
| IL-22 dimer 10 μg/kg, IV | 402 | 67 |
| IL-22 dimer 30 μg/kg, IV | 2355 | 393 |
| IL-22 dimer 45 μg/kg, IV | 3194 | 532 |

*indicating average value of placebo group b. C-Reactive Protein

The levels of C-reactive protein (CRP) were measured using immunity transmission turbidity.

Figure 8B:
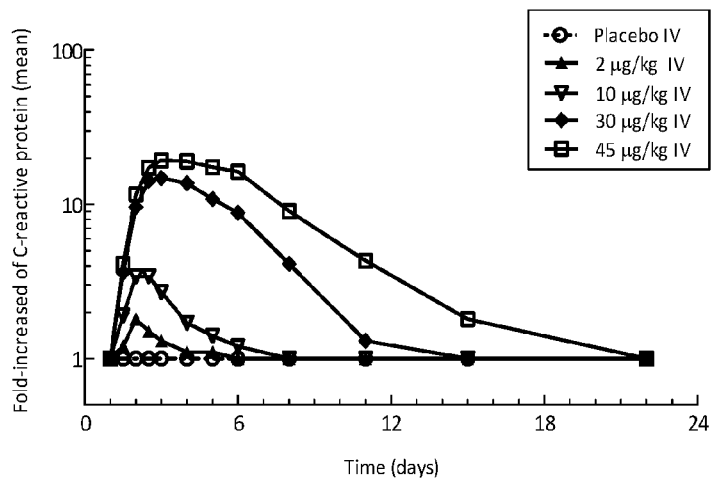
FIG. 8B shows the changes of the serum levels of C-reactive protein in human with the time after intravenous administration of IL-22 dimer.

As shown in FIG. 8B, the IV administration of IL-22 dimer significantly increased the serum concentration of C-reactive protein compared to the placebo group.

c. Triglyceride

The changes of serum triglycerides prior to and post the administration were detected using automatic blood biochemistry analyzer.

Figure 8C:
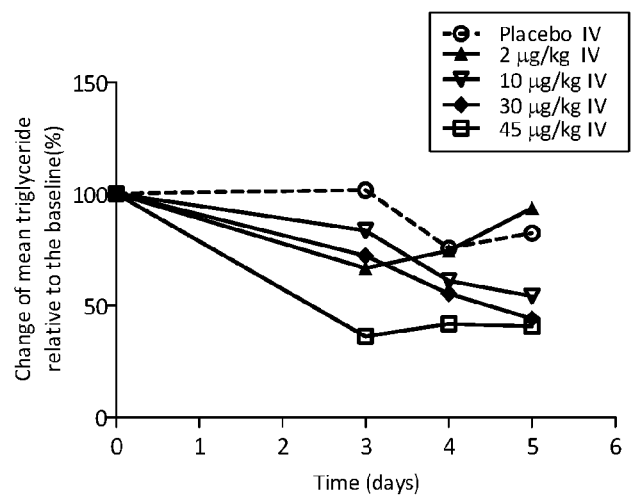
FIG. 8C shows the changes of the serum levels of triglyceride in human with the time after intravenous administration of IL-22 dimer.

As shown in FIG. 8C, the IV administration of IL-22 dimer significantly reduced the serum levels of triglyceride, exhibiting an obvious dose response relationship compared to the placebo group.

d. Cytokine Assay

The serum samples of placebo group and IL-22 dimer 45 μ/kg IV group were collected before the administration and at 24, 48 hrs after the administration, and were measured using Proteome Profiler Arrays-Human Cytokine Array Panel A (Cat. No. ARY005, R&D systems) to obtain the levels of various cytokines. The PBMCs (human Peripheral Blood Mononuclear Cells) were treated with 50 ng/mL PMA (phorbol myristate acetate) for 24 hrs and then the supernatant was used as a positive control. 200 μL of each serum samples was loaded and measured following the kit's instruction.

Figure 8D:
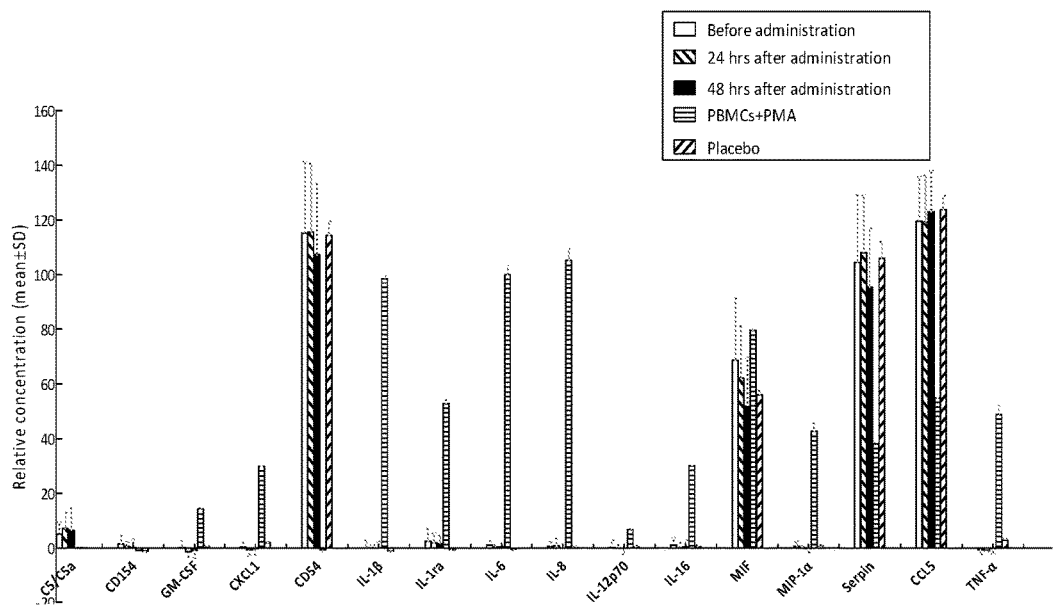
FIG. 8D shows the effect on the serum levels of various cytokines in human with the time after intravenous administration of IL-22 dimer.

As shown in FIG. 8D, the levels of inflammatory cytokines such as TNFα, IL-6, IL-1β, IL-8, etc were markedly increased in the positive control(PBMCs+PMA). Showing a similar profile to the placebo group, the levels of CD54, MIF, Serpin E1 and CCL5 were relatively higher for the serum samples taken at 24 and 48 hrs after the administration in the IL-22 dimer 45 μ/kg IV group, and the levels of inflammatory cytokines such as TNFα, IL-6, IL-1β, IL-8 did not markedly change compared to that of serum samples taken prior to the administration. These demonstrated that the administration of IL-22 dimer does not lead to increased levels of serum inflammatory cytokines.

Example 6

Preventive and Therapeutic Efficacy of IL-22 or IL-22 Dimer in Rat Model of Acute Pancreatitis Induced by Retrograde Injection of Sodium Taurocholate into the Biliopancreatic Duct Acute pancreatitis model induced by retrograde injection of sodium taurocholate into the biliopancreatic duct, has been widely used to assess the pathogenesis of bile reflux pancreatitis and the efficacy of a medicament. In this experiment, the rat model of acute pancreatitis was produced by retrograde injection of 0.1 mL/100 g 3.5% sodium taurocholate into the biliopancreatic duct.

SD rats were randomly divided into 3 groups:

Model control group (n=6), received a single intravenous injection of equal volume of solvent two hrs before surgery.

IL-22 monomer 40 μ/kg group (n=7), received a single intravenous injection of 40 μ/kg recombinant human IL-22 (rhIL-22) two hrs before surgery.

IL-22 dimer 100 μ/kg group (n=7), received a single intravenous injection of 100 μ/kg IL-22 dimer (comprising an equal molar IL-22 molecule dosage in comparison to IL-22 monomer 40 μ/kg group) two hrs before surgery.

The IL-22 dimer consisted of two monomeric subunits each comprising a sequence shown in SEQ ID NO: 4.

The animals were given free access to water and fasted for 12 hrs before surgery.

Surgical Procedures:

Rats in the model group were anaesthetized with diethyl ether. The abdomen was opened by a midline incision, the duodenum and common bile duct were identified, then the common bile duct was temporarily occluded at the confluence of hepatic hilus hepatic duct using a microvascular clamp. Upon finding a mesenterium avascular area at lateral wall of duodenum, a 0.4 size needle was used to puncture and sideling insert into the bile-pancreatic duct in the mesenterium avascular area, and then pulled out. A polyethylene(PE) 10 tube was then inserted into the bile-pancreatic duct along the duodenal papilla for 8-10 mm via the hole, and fixed to avoid dropping out. 3.5% sodium taurocholate (0.1 mL/100 g) was slowly infused in a retrograde way, and the needle core was kept staying for 8 mins after injection. Upon removing the polyethylene tube and microvascular clamp, the abdomen was closed. Rats were given free access to food and water after surgery. At 12 hrs after surgery, blood samples were taken from rat orbital venous plexus, and then the serum was separated by centrifuging. The serum levels of amylase and lipase were measured.

The animals were sacrificed 48 hrs after surgery. The pancreas tissues of rats were taken and fixed in 10% formalin solution. Tissues at head, middle, and tail of the pancreas were sliced and made into 3 μm paraffin sections, respectively. The sections were stained with HE, and the pathological changes were observed under a light microscope. Scores of edema, necrosis, hemorrhage, inflammatory cell infiltration, etc were evaluated in a double blind fashion, according to the scales of Schmidt (Schmidt et al. Ann Surg, 1992, 215(1):44-56). Scoring of 3 sections including the head, middle, and tail of the pancreas for each rat was performed.

Figure 9A:
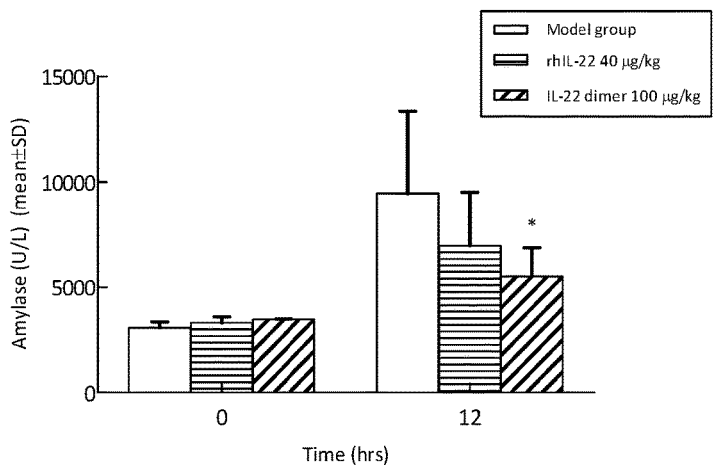
FIG. 9A shows the effect of IL-22 and IL-22 dimer on serum amylase levels in pancreatitis model rats.
Figure 9B:
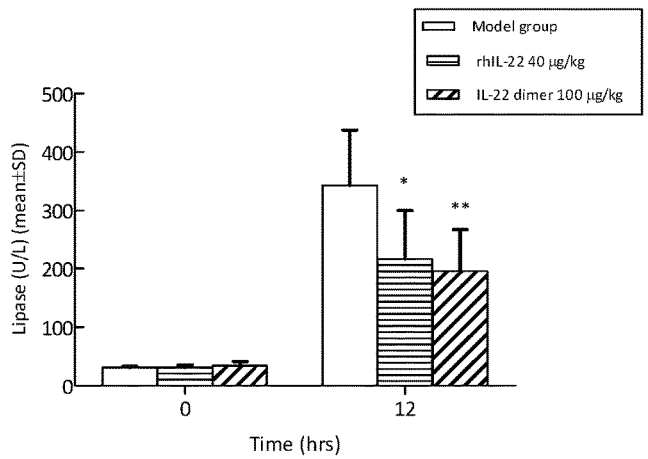
FIG. 9B shows the effect of IL-22 and IL-22 dimer on serum lypase levels in pancreatitis model rats.

Results:

The pancreatitis animal model was successfully established, as evidenced by a significant elevation in serum levels of amylase and lipase. As shown in FIGS. 9A and 9B, compared to the model group, IL-22 monomer has a trend to decrease the serum levels of amylase, but there was no significant difference. The serum levels of amylase were significantly decreased after the IL-22 dimer treatment ($P=0.03$). Compared to the model group, the serum levels of lipase were significantly decreased ($P=0.03$) after the IL-22 monomer treatment, whereas the serum levels of lipase were significantly decreased after the IL-22 dimer treatment ($P=0.008$). It is worth noting that, at equal molar IL-22 dosage, the IL-22 dimer was therapeutically effective in pancreatitis rat model, and the efficacy was better than that of IL-22. Under a microscope, obvious edema, a mass of inflammatory cell infiltration, necrosis of partial acinar cell and adipose cell, and a small amount of hemorrhage were observed in the pancreatic tissues of model group. IL-22 dimer can significantly improve the pathology score in animals of pancreatitis, showing a protective role on pancreas. At equal molar IL-22 dosage, no significant protective effect of IL-22 monomer on pancreas was observed.

TABLE 5

The pathology scores of pancreatic tissue in rats

| | Edema | Inflammatory cell infiltration | Necrosis of acinar cell | Hemorrhage | Necrosis of adipose cell | Total |
|---|---|---|---|---|---|---|
| Model group | 6.2 ± 1.8 | 7.0 ± 1.2 | 3.8 ± 2.2 | 2.4 ± 2.1 | 1.4 ± 0.9 | 20.8 ± 4.0 |
| IL-22 monomer group 40 μg/kg | 7.4 ± 1.7 | 5.7 ± 1.6 | 2.4 ± 1.7 | 3.7 ± 3.4 | 0.9 ± 0.7 | 20.1 ± 4.0 |
| IL-22 dimer group 100 μg/kg | 4.3 ± 2.7$^b$ | 5.7 ± 2.3 | 2.3 ± 0.5 | 2.3 ± 2.1 | 0.5 ± 0.8 | 15.2 ± 3.8$^{ab}$ |

$^a$indicating $P < 0.05$ compared to the model group.
$^b$indicating $P < 0.05$ compared to the IL-22 monomer group.

All references mentioned in the present invention are incorporated herein by reference as if each of those references has been incorporated by reference individually. Although the description referred to particular embodiments, it will be clear to a person skilled in the art that the present invention may be practiced with variation of these specific details. Hence this invention should not be construed as limited to the embodiments set forth herein.

We claim:

1. A method of treating pancreatitis in a human individual, comprising intravenously administering to the human individual an effective amount of an IL-22 dimer, wherein the IL-22 dimer comprises two monomeric subunits, wherein each monomeric subunit comprises IL-22 fused to a dimerization domain, and wherein the amount of the IL-22 dimer is about 2 µg/kg to about 200 µg/kg.

2. The method of claim 1, wherein the IL-22 dimer is administered at the amount of about 5 µg/kg to about 80 µg/kg.

3. The method of claim 1, wherein the IL-22 dimer is administered at the amount of about 10 µg/kg to about 45 µg/kg.

4. The method of claim 1, wherein the IL-22 dimer is administered no more than once a week.

5. The method of claim 1, wherein the IL-22 dimer is administered no more than once a month.

6. The method of claim 1, wherein the IL-22 dimer is administered no more than once every three months.

7. The method of claim 1, wherein each monomeric subunit comprises IL-22 linked to the dimerization domain via a linker sequence.

8. The method of claim 7, wherein the linker sequence is about 6 to about 30 amino acids.

9. The method of claim 8, wherein the linker sequence comprises the sequence of SEQ ID NO: 1.

10. The method of claim 1, wherein the dimerization domain comprises at least two cysteines capable of forming intermolecular disulfide bonds.

11. The method of claim 1, wherein the dimerization domain comprises at least a portion of an Fc region.

12. The method of claim 11, wherein the Fc region comprises CH2 and CH3 domains.

13. The method of claim 12, wherein the Fc region comprises the sequence of SEQ ID NO:2 or SEQ ID NO:9.

14. The method of claim 1, wherein IL-22 of each monomeric subunit has the sequence of SEQ ID NO:3.

15. The method of claim 1, wherein each monomeric subunit comprises an amino acid sequence selected from the group consisting of SEQ ID NO:4 and SEQ ID NOs: 6-8.

16. The method of claim 1, wherein the pancreatitis is selected from the group consisting of: acute pancreatitis, chronic pancreatitis, alcoholic pancreatitis, recurrent pancreatitis, bile reflux pancreatitis, interstitial pancreatitis, necrotizing pancreatitis, and post endoscopic retrograde cholangiopancreatography (ERCP) pancreatitis.

* * * * *

SEQUENCE LISTING

```
<160> NUMBER OF SEQ ID NOS: 10

<210> SEQ ID NO 1
<211> LENGTH: 16
<212> TYPE: PRT
<213> ORGANISM: Artificial sequence
<220> FEATURE:
<221> NAME/KEY: MISC FEATURE
<223> OTHER INFORMATION: short peptide

<400> SEQUENCE: 1

Gly Ser Gly Gly Gly Ser Gly Gly Gly Gly Ser Gly Gly Gly Gly Ser
1               5                   10                  15

<210> SEQ ID NO 2
<211> LENGTH: 223
<212> TYPE: PRT
<213> ORGANISM: Artificial sequence
<220> FEATURE:
<221> NAME/KEY: MISC FEATURE
<223> OTHER INFORMATION: IgG2 Fc
```

```
<400> SEQUENCE: 2

Val Glu Cys Pro Pro Cys Pro Ala Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
                100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
        210                 215                 220

<210> SEQ ID NO 3
<211> LENGTH: 146
<212> TYPE: PRT
<213> ORGANISM: Artificial sequence
<220> FEATURE:
<221> NAME/KEY: MISC FEATURE
<223> OTHER INFORMATION: IL-22

<400> SEQUENCE: 3

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
            35                  40                  45

Gly Val Ser Met Ser Glu Arg Cys Tyr Leu Met Lys Gln Val Leu Asn
        50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125
```

```
Lys Ala Ile Gly Glu Leu Asp Leu Leu Phe Met Ser Leu Arg Asn Ala
            130                 135                 140

Cys Ile
145

<210> SEQ ID NO 4
<211> LENGTH: 385
<212> TYPE: PRT
<213> ORGANISM: Artificial sequence
<220> FEATURE:
<221> NAME/KEY: MISC FEATURE
<223> OTHER INFORMATION: IL-22 -linker -IgG2 Fc

<400> SEQUENCE: 4

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
            35                  40                  45

Gly Val Ser Met Ser Glu Arg Cys Tyr Leu Met Lys Gln Val Leu Asn
50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
            115                 120                 125

Lys Ala Ile Gly Glu Leu Asp Leu Leu Phe Met Ser Leu Arg Asn Ala
130                 135                 140

Cys Ile Gly Ser Gly Gly Ser Gly Gly Gly Ser Gly Gly Gly
145                 150                 155                 160

Gly Ser Val Glu Cys Pro Pro Cys Pro Ala Pro Pro Val Ala Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
            195                 200                 205

Pro Glu Val Gln Phe Asn Trp Tyr Val Asp Gly Val Glu Val His Asn
        210                 215                 220

Ala Lys Thr Lys Pro Arg Glu Glu Gln Phe Asn Ser Thr Phe Arg Val
225                 230                 235                 240

Val Ser Val Leu Thr Val Val His Gln Asp Trp Leu Asn Gly Lys Glu
                245                 250                 255

Tyr Lys Cys Lys Val Ser Asn Lys Gly Leu Pro Ala Ser Ile Glu Lys
            260                 265                 270

Thr Ile Ser Lys Thr Lys Gly Gln Pro Arg Glu Pro Gln Val Tyr Thr
            275                 280                 285

Leu Pro Pro Ser Arg Glu Glu Met Thr Lys Asn Gln Val Ser Leu Thr
        290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Met Leu
                325                 330                 335
```

Asp Ser Asp Gly Ser Phe Phe Leu Tyr Ser Lys Leu Thr Val Asp Lys
                340                 345                 350

Ser Arg Trp Gln Gln Gly Asn Val Phe Ser Cys Ser Val Met His Glu
355                 360                 365

Ala Leu His Asn His Tyr Thr Gln Lys Ser Leu Ser Leu Ser Pro Gly
    370                 375                 380

Lys
385

<210> SEQ ID NO 5
<211> LENGTH: 308
<212> TYPE: PRT
<213> ORGANISM: Artificial sequence
<220> FEATURE:
<221> NAME/KEY: MISC FEATURE
<223> OTHER INFORMATION: IL-22 -linker -IL-22

<400> SEQUENCE: 5

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Gly Ser Gly Gly Ser Gly Gly Gly Ser Gly Gly Gly
145                 150                 155                 160

Gly Ser Ala Pro Ile Ser Ser His Cys Arg Leu Asp Lys Ser Asn Phe
                165                 170                 175

Gln Gln Pro Tyr Ile Thr Asn Arg Thr Phe Met Leu Ala Lys Glu Ala
            180                 185                 190

Ser Leu Ala Asp Asn Asn Thr Asp Val Arg Leu Ile Gly Glu Lys Leu
        195                 200                 205

Phe His Gly Val Ser Met Ser Glu Arg Cys Tyr Leu Met Lys Gln Val
    210                 215                 220

Leu Asn Phe Thr Leu Glu Glu Val Leu Phe Pro Gln Ser Asp Arg Phe
225                 230                 235                 240

Gln Pro Tyr Met Gln Glu Val Val Pro Phe Leu Ala Arg Leu Ser Asn
                245                 250                 255

Arg Leu Ser Thr Cys His Ile Glu Gly Asp Asp Leu His Ile Gln Arg
            260                 265                 270

Asn Val Gln Lys Leu Lys Asp Thr Val Lys Lys Leu Gly Glu Ser Gly
        275                 280                 285

Glu Ile Lys Ala Ile Gly Glu Leu Asp Leu Leu Phe Met Ser Leu Arg
            290                 295                 300

Asn Ala Cys Ile
305

<210> SEQ ID NO 6
<211> LENGTH: 375
<212> TYPE: PRT
<213> ORGANISM: Artificial sequence
<220> FEATURE:
<221> NAME/KEY: MISC FEATURE
<223> OTHER INFORMATION: IL-22-linker-IgG2 Fc

<400> SEQUENCE: 6

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Ala Ser Thr Lys Gly Pro Val Glu Cys Pro Pro Cys Pro Ala
145                 150                 155                 160

Pro Pro Val Ala Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Gln Phe Asn Trp Tyr Val Asp
        195                 200                 205

Gly Val Glu Val His Asn Ala Lys Thr Lys Pro Arg Glu Glu Gln Phe
    210                 215                 220

Asn Ser Thr Phe Arg Val Val Ser Val Leu Thr Val Val His Gln Asp
225                 230                 235                 240

Trp Leu Asn Gly Lys Glu Tyr Lys Cys Lys Val Ser Asn Lys Gly Leu
                245                 250                 255

Pro Ala Ser Ile Glu Lys Thr Ile Ser Lys Thr Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Met Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
                340                 345                 350

Cys Ser Val Met His Glu Ala Leu His Asn His Tyr Thr Gln Lys Ser
            355                 360                 365

Leu Ser Leu Ser Pro Gly Lys
    370                 375

<210> SEQ ID NO 7
<211> LENGTH: 385
<212> TYPE: PRT
<213> ORGANISM: Artificial sequence
<220> FEATURE:
<221> NAME/KEY: MISC FEATURE
<223> OTHER INFORMATION: IgG2 Fc-linker- IL-2

<400> SEQUENCE: 7

Val Glu Cys Pro Pro Cys Pro Ala Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
    115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
    195                 200                 205

His Asn His Tyr Thr Gln Lys Ser Leu Ser Leu Ser Pro Gly Lys Gly
210                 215                 220

Ser Gly Gly Gly Ser Gly Gly Gly Ser Gly Gly Gly Gly Ser Ala
225                 230                 235                 240

Pro Ile Ser Ser His Cys Arg Leu Asp Lys Ser Asn Phe Gln Gln Pro
                245                 250                 255

Tyr Ile Thr Asn Arg Thr Phe Met Leu Ala Lys Glu Ala Ser Leu Ala
            260                 265                 270

Asp Asn Asn Thr Asp Val Arg Leu Ile Gly Glu Lys Leu Phe His Gly
    275                 280                 285

Val Ser Met Ser Glu Arg Cys Tyr Leu Met Lys Gln Val Leu Asn Phe
290                 295                 300

Thr Leu Glu Glu Val Leu Phe Pro Gln Ser Asp Arg Phe Gln Pro Tyr
305                 310                 315                 320

```
Met Gln Glu Val Val Pro Phe Leu Ala Arg Leu Ser Asn Arg Leu Ser
                325                 330                 335
Thr Cys His Ile Glu Gly Asp Asp Leu His Ile Gln Arg Asn Val Gln
            340                 345                 350
Lys Leu Lys Asp Thr Val Lys Lys Leu Gly Glu Ser Gly Glu Ile Lys
        355                 360                 365
Ala Ile Gly Glu Leu Asp Leu Leu Phe Met Ser Leu Arg Asn Ala Cys
    370                 375                 380
Ile
385

<210> SEQ ID NO 8
<211> LENGTH: 375
<212> TYPE: PRT
<213> ORGANISM: Artificial sequence
<220> FEATURE:
<221> NAME/KEY: MISC FEATURE
<223> OTHER INFORMATION: IgG2 Fc-linker- IL-22

<400> SEQUENCE: 8

Val Glu Cys Pro Pro Cys Pro Ala Pro Pro Val Ala Gly Pro Ser Val
1               5                   10                  15
Phe Leu Phe Pro Pro Lys Pro Lys Asp Thr Leu Met Ile Ser Arg Thr
                20                  25                  30
Pro Glu Val Thr Cys Val Val Val Asp Val Ser His Glu Asp Pro Glu
            35                  40                  45
Val Gln Phe Asn Trp Tyr Val Asp Gly Val Glu Val His Asn Ala Lys
        50                  55                  60
Thr Lys Pro Arg Glu Glu Gln Phe Asn Ser Thr Phe Arg Val Val Ser
65                  70                  75                  80
Val Leu Thr Val Val His Gln Asp Trp Leu Asn Gly Lys Glu Tyr Lys
                85                  90                  95
Cys Lys Val Ser Asn Lys Gly Leu Pro Ala Ser Ile Glu Lys Thr Ile
                100                 105                 110
Ser Lys Thr Lys Gly Gln Pro Arg Glu Pro Gln Val Tyr Thr Leu Pro
        115                 120                 125
Pro Ser Arg Glu Glu Met Thr Lys Asn Gln Val Ser Leu Thr Cys Leu
130                 135                 140
Val Lys Gly Phe Tyr Pro Ser Asp Ile Ala Val Glu Trp Glu Ser Asn
145                 150                 155                 160
Gly Gln Pro Glu Asn Asn Tyr Lys Thr Thr Pro Pro Met Leu Asp Ser
                165                 170                 175
Asp Gly Ser Phe Phe Leu Tyr Ser Lys Leu Thr Val Asp Lys Ser Arg
            180                 185                 190
Trp Gln Gln Gly Asn Val Phe Ser Cys Ser Val Met His Glu Ala Leu
        195                 200                 205
His Asn His Tyr Thr Gln Lys Ser Leu Ser Leu Ser Pro Gly Lys Ala
    210                 215                 220
Ser Thr Lys Gly Pro Ala Pro Ile Ser Ser His Cys Arg Leu Asp Lys
225                 230                 235                 240
Ser Asn Phe Gln Gln Pro Tyr Ile Thr Asn Arg Thr Phe Met Leu Ala
                245                 250                 255
Lys Glu Ala Ser Leu Ala Asp Asn Asn Thr Asp Val Arg Leu Ile Gly
            260                 265                 270
Glu Lys Leu Phe His Gly Val Ser Met Ser Glu Arg Cys Tyr Leu Met
        275                 280                 285
```

-continued

```
Lys Gln Val Leu Asn Phe Thr Leu Glu Glu Val Leu Phe Pro Gln Ser
        290                 295                 300

Asp Arg Phe Gln Pro Tyr Met Gln Glu Val Val Pro Phe Leu Ala Arg
305                 310                 315                 320

Leu Ser Asn Arg Leu Ser Thr Cys His Ile Glu Gly Asp Asp Leu His
                325                 330                 335

Ile Gln Arg Asn Val Gln Lys Leu Lys Asp Thr Val Lys Lys Leu Gly
                340                 345                 350

Glu Ser Gly Glu Ile Lys Ala Ile Gly Glu Leu Asp Leu Leu Phe Met
            355                 360                 365

Ser Leu Arg Asn Ala Cys Ile
        370                 375
```

<210> SEQ ID NO 9
<211> LENGTH: 228
<212> TYPE: PRT
<213> ORGANISM: homo sapiens

<400> SEQUENCE: 9

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
                100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

<210> SEQ ID NO 10
<211> LENGTH: 6
<212> TYPE: PRT
<213> ORGANISM: Artificial sequence
<220> FEATURE:
<221> NAME/KEY: MISC FEATURE
<223> OTHER INFORMATION: short peptide

```
<400> SEQUENCE: 10

Ala Ser Thr Lys Gly Pro
1               5
```